(12) United States Patent
Schiff

(10) Patent No.: US 8,588,899 B2
(45) Date of Patent: Nov. 19, 2013

(54) MODEL BASED CONTROL OF PARKINSON'S DISEASE

(76) Inventor: Steven John Schiff, State College, PA (US)

( * ) Notice: Subject to any disclaimer, the term of this patent is extended or adjusted under 35 U.S.C. 154(b) by 0 days.

(21) Appl. No.: 13/636,684

(22) PCT Filed: Mar. 23, 2011

(86) PCT No.: PCT/US2011/000534
§ 371 (c)(1),
(2), (4) Date: Nov. 29, 2012

(87) PCT Pub. No.: WO2011/119224
PCT Pub. Date: Sep. 29, 2011

(65) Prior Publication Data
US 2013/0102919 A1     Apr. 25, 2013

Related U.S. Application Data

(60) Provisional application No. 61/317,041, filed on Mar. 24, 2010.

(51) Int. Cl.
*A61B 5/04* (2006.01)

(52) U.S. Cl.
USPC .............................. 600/544; 706/15

(58) Field of Classification Search
USPC ................. 600/544, 545; 607/45, 46
See application file for complete search history.

(56) References Cited

U.S. PATENT DOCUMENTS

| | | |
|---|---|---|
| 2005/0124848 A1 | 6/2005 | Holzner |
| 2006/0217781 A1 * | 9/2006 | John ................. 607/45 |
| 2007/0067003 A1 | 3/2007 | Sanchez et al. |
| 2007/0213786 A1 | 9/2007 | Sackellares et al. |
| 2008/0027651 A1 * | 1/2008 | Siekmeier et al. ............. 702/19 |

OTHER PUBLICATIONS

Frankemolle, A. et al. "Reversing cognitive-motor impairments in Parkinson's disease patients using a computational modelling approach to deep brain stimulation programming." Brain: A Journal of Neurology, 2010: 133, pp. 746-761.*
Li et al., "Unscented Kalman Filter for Brain-Machine Interfaces," PLoS ONE. Jul. 15, 2009, vol. 4, Issue 7, e6243.
Evensen, et al., "An Ensemble Kalman Smoother for Nonlinear Dynamics," Monthly Weather Review, Jun. 2000, vol. 128, Issue 6, pp. 1852-1867.

* cited by examiner

*Primary Examiner* — Patricia Mallari
*Assistant Examiner* — Etsub Berhanu
(74) *Attorney, Agent, or Firm* — Barbara E. Johnson, Esq.

(57) ABSTRACT

The present invention relates to a novel means to use a fundamental model of the parts of the brain that are dysfunctional in Parkinson's disease, and related dynamical diseases of the brain, as part of a feedback control system to modulate the signs and symptoms of disease. Fundamental computational models that embody our knowledge of the anatomy, neurons, and dynamics of the parts of the brain we wish to control, and use those models to reconstruct what is inaccessible to our measurements. Through emulation the controller synchronizes to the parts of the brain we wish to observe and track. By passing simultaneous control pulses to both the model controller, as well as the brain, we control both the model and the brain. The detailed framework to embed fundamental models of the brain within a control scheme to control symptoms of Parkinsons and related dynamical diseases of the brain are disclosed.

4 Claims, 12 Drawing Sheets

A Proportional Control

B Proportional Control with Observer

C Kalman Observer Control

D Kalman Observer Differential Control

MODEL BASED CONTROL OF PARKINSON'S DISEASE

This application claims the benefit of U.S. Provisional Patent Application Ser. No. 61/317,041, filed 24 Mar. 2010, which is incorporated herein by reference.

BACKGROUND OF THE INVENTION

Field of the Invention

The present invention relates to a novel means to use a fundamental model of the parts of the brain that are dysfunctional in Parkinson's disease, and related movement disorders, as part of a feedback control system to modulate the signs and symptoms of Parkinson's disease.

Envisioning feedback modulation of neural circuitry is not new in treating diseases of the brain, but all prior art has relied upon empirical methods of signal processing the data that is sensed from recording methods such as electrodes or other sensors.

What is unique about this present approach is that we take one or more computational models that embody our knowledge of the dynamics of the parts of the brain we wish to control, and use those models to reconstruct what is inaccessible to our measurements. The controller thereby synchronizes to the parts of the brain we wish to observe and track. By passing simultaneous control pulses to both the model controller, as well as the brain, the controller synchronizes to the brain, and we control both the model and the brain.

Similar controllers are in use in probabilistic robotics such as airplane autolanders. But the availability of models to control diseases of the brain are only a relatively recent phenomena, with Parkinson's disease modeling becoming sophisticated enough to consider only by 2002-2004. The availability of ensemble control filters capable of assimilating data into such complex nonlinear models has only been available since the mid 1990s. The fusion of computational brain models with nonlinear ensemble filters to control brain circuitry in the manner we propose has never before been done.

Dynamical diseases are diseases characterized by the operation of a basically normal control system in a region of physiological parameters that produces pathological behavior ["Oscillation and chaos in physiological control systems" (Mackey, M. C. and Glass, L.) (1977) *Science* 197(4300): 287-289]. Dynamical diseases of the brain are those where the symptoms are created by abnormal patterns of activity within neuronal networks [Milton, J. and Jung, P., editors (2003) *Epilepsy as a Dynamical Disease* Springer-Verlag Berlin]. This invention proposes fusing fundamental computational models of brain network dynamics with ensemble control filters to direct neural stimulation for the treatment of dynamical brain disease.

Modern control engineering uses computational models of a system (the airframe's equations of motion, or the convection physics of the atmosphere in the case of weather prediction) to perform the assimilation of observable data, the reconstruction of unobservable variables in the system state, the estimation of parameters (constant or slowly changing variables), and the short-term prediction of the system state. This sequence is then followed by the next iteration of data assimilation, and so forth. Biology and medicine were cut out of interacting with such control engineering until computational models were developed of sufficient applicability to warrant use.

Modern (model-based) control engineering had its roots in the control of linear (or linearizable) systems. In parallel with the development of the early US space program, Kalman ["A new approach to linear filtering and prediction problems" (Kalman, R. E.) (1960) *Transactions of the ASME-Journal of Basic Engineering* 82, series D:35-45] devised a filter, which for linear systems is a maximum likelihood estimator, which gives the optimal tracking of system state and optimal calculation of control signals to change such states. The dual theorems of observability and reachability for such systems have been considered one of the most useful developments in mathematics of the 20th century [Casti, J. L. (2000) *Five more golden rules: knots, codes, chaos, and other great theories of 20th century mathematics* Wiley New York]. Observability and reachability theorems essentially state that if you can observe a system's state variables, you can optimally control it (to reach a given state).

Kalman's original filter was fast but had its limits. Nonlinear models were handled for several decades by linearizing equations about the operating points of the system state (extended Kalman filter, EKF). Such linearization is notoriously unreliable in many systems, often dramatically shown in the simple conversion of polar to Cartesian coordinates in range locating systems (sine and cosines do not linearize well). Biology often regulates its systems far removed from the simple homeostasis of the early 20th Century work of Walter Cannon [Cannon, W. B. (1932) *The Wisdom of the Body* W. W. Norton New York]—witness the pulsatile secretion of parathormone ["Predicting pth pulses and patterns in osteoporosis (editorial)" (Schiff, S. J. and Deftos, L.) (1995) *Journal of Clinical Investigation* 95:2433-2434], the contractility of the heart, or the firing of a neuronal action potential. Prior to the late 1990s, the only solution to such serious nonlinearities would be to employ Monte Carlo techniques (such as particle filters) to iterate an ensemble of system states by one-by-one iterating each point in an estimated distribution of states through the nonlinear equations (see ["Modified particle filter methods for assimilating lagrangian data into a point-vortex model" (Spiller, E. T. and Budhiraja, A. and Ide, K. and Jones, C. K. R. T.) (2008) *Physica D: Nonlinear Phenomena* 237: 1498-1506] for detailed discussion of particle filtering vs the extended Kalman filter in nonlinear systems). Particle filters have been explored to some degree in biological systems, but their inherent inefficiency renders them at present almost entirely inapplicable to real-time observation and control.

In the late 1990s, Julier and Uhlman ["A new extension of the Kalman filter to nonlinear systems" (Julier, Simon J. and Uhlmann, Jeffery K.) (1997a) *SPIE* 3068:182-193, "A consistent, debiased method for converting between polar and Cartesian coordinate systems" (Julier, Simon J. and Uhlmann, Jeffery K.) (1997b) *SPIE* 3086:110-121] published a highly efficient method of parameterizing state uncertainty for nonlinear systems that they termed the unscented Kalman filter (UKF). Within a decade, it has become the mainstay of the robotics scientist [Thrun, S., Burgard, W., and Fox, D. (2005) *Probabilistic robotics* MIT Press Cambridge, Mass]. In parallel, from within an almost completely separate literature, numerical meteorology developed their ensemble Kalman filter (EnKF) and its variants ["Sequential data assimilation with a nonlinear quasi-geostrophic model using Monte Carlo methods to forecast error statistics" (Evensen, Geir) (1994) *Journal of Geophysical Research* 99:10143-10162, "An ensemble Kalman smoother for nonlinear dynamics" (Evensen, G. and van Leeuwen, P. J.) (2000) *Monthly Weather Review* 128(6):1852-1867]. Both UKF and EnKF do the same thing. They permit us to fly an airplane in real time, and to iterate huge convection models of the atmosphere several times per day, using nonlinear models with unprecedented efficiency and accuracy.

In 2004, Voss and colleagues demonstrated that action potential dynamics of single neurons might be amenable to tracking with such a nonlinear UKF ["Nonlinear dynamical system identification from uncertain and indirect measurements" (Voss, H. U. and Timmer, J. and Kurths, J.) (2004) *International Journal of Bifurcation and Chaos* 14(6):1905-1933].

We have now spent several years exploring the implications of the Voss et al work. We first extended Voss's approach to a framework for the analysis of spatiotemporal data from cortical voltage sensitive dye imaging experiments. We showed that such an approach was not only feasible, but that it was robust to large amounts of measurement noise. By using an observer system run in parallel with the experimental system, we could very significantly reduce the energy required to control such a system with electrical feedback ["Kalman filter control of a model of spatiotemporal cortical dynamics" (Schiff, Steven J and Sauer, Tim) (2008) *J Neural Eng* 5(1):1-8]. Voss, as did we, had employed reduced simplified models of neurons (either Fitzhugh-Nagumo or Wilson-Cowan equations).

We then adapted this strategy to work with biophysically realistic models of neurons. We showed that not only could the foundational Hodgkin-Huxley ionic equations be incorporated into such a control framework, but that an UKF strategy was rather striking in its ability to accurately reconstruct the entire set of Hodgkin-Huxley conductance and rate variables given only voltage measurements ["Tracking and control of neuronal hodgkin-huxley dynamics" (Ullah, G. and Schiff, S. J.) (2009b) *Physical Review* E79(4):40901]. Our guess is that such success must be related to the intrinsic independence of ionic currents and time constants present in these equations, and of course in the real neurons upon which they are based—the symmetries are insufficient to impair the reconstruction.

Hodgkin and Huxley left out that these neuronal dynamics were intimately coupled to complex metabolic ion dynamics both extracellularly and coupled to glia, and we have worked out a comprehensive computational framework to account for the dynamics of potassium flux into and out of neurons and glia, as well as the effect of such flux dynamics on the excitability of neuronal networks ["The influence of sodium and potassium dynamics on excitability, seizures, and the stability of persistent states: I. single neuron dynamics" (Cressman, J. R. and Ullah, G. and Ziburkus, J. and Schiff, S. J. and Barreto, E.) (2009) *Journal of computational neuroscience* 26(2):159-170, "The influence of sodium and potassium dynamics on excitability, seizures, and the stability of persistent states: Ii. network and glial dynamics" (Ullah, G. and Cressman Jr, J. R. and Barreto, E. and Schiff, S. J.) (2009a) *Journal of Computational Neuroscience* 26(2):171-183]. We demonstrated in our models that such ionic dynamics could account for major components of the phenomenology that we observe experimentally in the dynamics of epileptic seizures.

We demonstrated that our control framework could readily incorporate such ionic dynamics as well. We showed a powerful way to perform dynamic clamp, using a more complete reconstruction of the cellular dynamics, rather than the more isolated conductance relationships customarily used ["Tracking and control of neuronal hodgkin-huxley dynamics" (Ullah, G. and Schiff, S. J.) (2009b) *Physical Review* E79(4):40901]. We also showed how to potentially incorporate this ionic framework to modulate seizure dynamics ["Tracking and control of neuronal hodgkin-huxley dynamics" (Ullah, G. and Schiff, S. J.) (2009b) *Physical Review* E79(4):40901].

Variability is profound in biology, whether from the genome, proteome, or species level [Kirschner, M. and Gerhart, J. C. (2005) *The Plausibility of Life* Yale University Press New Haven]. Compounding the difficulties with variability, the complexity of all biological systems far surpasses the details in our models. All models are bad to some degree (even that of a simple pendulum), but our models of biological cell, network, and organismal dynamics are terrible by comparison with, for instance, our models of airframes. We therefore began to develop a comprehensive strategy to directly deal with model inadequacy in such biological systems. We showed that we can, as part of our control frameworks, construct a locally optimized set of mean parameters that we term the consensus set. We have recently demonstrated our ability to track the dynamics from real spatiotemporal data from our brain experiments, using a local consensus set, and shown that our tracking errors converge to unexpected accuracy ["Data assimilation for heterogeneous networks: the consensus set" (Sauer, Timothy D and Schiff, Steven J) (2009) *Phys Rev E Stat Nonlin Soft Matter Phys* 79(5 Pt 1):051909]. Such a strategy can be broken up to local tessellations of networks when complexity demands this, and there are new rigorous EnKF tessellation methods in the numerical weather prediction literature ["Estimating the state of large spatio-temporally chaotic systems" (Ott, E. and Hunt, B R and Szunyogh, I. and Zimin, A V and Kostelich, E J and Corazza, M. and Kalnay, E. and Patil, D J and Yorke, J A) (2004) *Physics Letters* A330(5):365-370] ideal for such use.

The implications of the consensus set are that we are now able to use a model network of sufficient complexity and connectivity to accurately observe a real brain network despite uncertainties in cell dynamics and connection topology. Our short-term prediction accuracy appears sufficient for control. This is a completely different situation from the customary strategy of model validation—where one assumes that the model is correct, and that only the parameters need to be fit. The identical situation was found in a recent physics application of local EnKF to fluid dynamics—the best parameters to use in a simplified model are not the most physical, but in recognition of model inadequacy, are the optimal ones to best track observed dynamics ["State and parameter estimation of spatiotemporally chaotic systems illustrated by an application to rayleigh-bénard convection" (Cornick, M. and Hunt, B. and Ott, E. and Kurtuldu, H. and Schatz, M. F.) (2009) *Chaos: An Interdisciplinary Journal of Nonlinear Science* 19:013108]. The best parameters to use for such tracking and control work can be (bio)physically meaningless. But the model dynamics are not meaningless. Our conjecture is that for much of biology, seeking model validation in control scenarios may be the wrong goal. Seeking models of sufficient complexity to accurately emulate and track the dynamics of the state of a biological system may be a more relevant strategy.

This is not just a matter of making better control devices for biological systems. We often consider that if we simply amass sufficient computer hardware and software, that we will be able to create large-scale models that would be faithful replicas of structures such as the brain. Were such a thing possible we would have much trouble gaining insight into out how it worked, but access to all relevant variables would be a valuable feature that we could never have in a real brain. Most important is the sheer mass of parts and components to model—this is a fundamental 'limits to knowledge' problem as eloquently discussed by Scott [Scott, A. (1995) *Stairway to the mind: the controversial new science of consciousness* Copernicus New York]. All of us, whether modeling for an underpowered implantable device, or for the world's most powerful supercomputer, need to deal with serious model inadequacy when faced with real biology and disease.

A further way to deal with model inadequacy inherent in complex biological systems is to formally parameterize the uncertainty ["Local ensemble Kalman filtering in the presence of model bias" (Baek, S. J. and Hunt, B. R. and Kalnay, E. and Ott, E. and Szunyogh, I.) (2006) *Tellus* A58(3):293-306]. One of the problems with the strategy of Baek and colleagues is that they optimized their uncertainty parameters as an augmented state as part of their ensemble Kalman filter. There is no need for this. It needlessly complicates the computations and slows them down, and may miss the optimal values of the uncertainty parameters. We can optimize such uncertainty parameters outside of the Kalman filter loops to improve the speed and accuracy of the model-based control of diseases such as Parkinson's disease.

All control filters, whether linear Kalman or nonlinear UKF/EnKF, are at their essence synchronization problems ["Synchronicity in predictive modelling: a new view of data assimilation" (Duane, G. S, and Tribbia, J. J. and Weiss, J. B.) (2006) *Nonlinear Processes in Geophysics* 13(6):601-612, "Data assimilation as synchronization of truth and model: Experiments with the three-variable lorenz system" (Yang, S. C. and Baker, D. and Li, H. and Cordes, K. and Huff, M. and Nagpal, G. and Okereke, E. and Villafañe, J. and Kalnay, E. and Duane, G. S.) (2006) *Journal of the Atmospheric Sciences* 63(9):2340-2354]. That is, a suitable control filter will synchronize to the natural system it is observing when its performance is good. It is now well established that nonlinear systems can synchronize, and when not identical, can nonlinearly synchronize—generalized synchronization ["Detecting dynamical interdependence and generalized synchrony through mutual prediction in a neural ensemble" (Schiff and So and Chang and Burke and Sauer) (1996) *Phys Rev E Stat Phys Plasmas Fluids Relat Interdiscip Topics* 54(6):6708-6724]. Our techniques of establishing such synchronization often have made use of knowing the equations from the systems involved, except for a special case—when auxiliary systems are used. It turns out that when identical model systems, with different initial conditions, are driven by the same signal from a potentially unknown system, that at a certain level of driving they can 'forget' their initial conditions and synchronize ["Weak and strong synchronization of chaos" (Pyragas, K.) (1996) *Physical Review* E54(5):4508-4511]. If you perturb one of the driven systems, it exponentially dissipates its perturbation and re-synchronizes to the other driven system. This means that if we use biological models of sufficient complexity, and perturb one of the identical copies intermittently, that we can both infer the presence of synchronization with the inadequately modeled biological system, and furthermore quantify the model inadequacy in real time. Such model inadequacy leads us to adjust our uncertainty in the tracking systems, through so-called covariance inflation ["Data assimilation as synchronization of truth and model: Experiments with the three-variable lorenz system" (Yang, S. C. and Baker, D. and Li, H. and Cordes, K. and Huff, M. and Nagpal, G. and Okereke, E. and Villafañe, J. and Kalnay, E. and Duane, G. S.) (2006) *Journal of the Atmospheric Sciences* 63(9):2340-2354, "Making forecasts for chaotic physical processes" (Christopher M. Danforth and James A. Yorke) (2006) *Physical Review Letters* 96:144102]. This gives us the ability to probe a complex biological system using synchronizing controllers—the closer we get to the underlying dynamics the closer the synchronization.

All of the above suggests that we are at the verge of a transformation in our capabilities of tracking and controlling brain dynamics in health and disease. This patent application will discuss a way of applying such knowledge to Parkinson's disease.

Overview of Parkinson's Disease

Parkinson's disease was first described by James Parkinson in a monograph published in 1817 [Parkinson, J. (1817) *An essay on the shaking palsy* Sherwood, Neely, and Jones London]. It is a degenerative neurological condition, and we attempt to digest the neurological manifestations of this disease into 4 key signs: tremor, rigidity, bradykinesia (slowness of movement), and postural instability.

We have learned a considerable amount about the neurobiology of Parkinson's disease since the 19th century, but we do not know how to prevent it, and all of our present day treatments remain palliative ["Parkinson's disease" (Andrew J Lees and John Hardy and Tamas Revesz) (2009) *The Lancet* 373(9680):2055-2066]. The discovery by Carlsson and colleagues that a precursor to dopamine in the brain could ameliorate the effects of dopamine depletion ["3,4-dihydroxyphenylalanine and 5-hydroxytryptophan as reserpine antagonists" (Carlsson, A. and Lindqvist, M. and Magnusson, T.) (1957) *Nature* 180:1200] led to successful medical therapy of Parkinson's disease with L-3,4-dihydroxyphenylalanine (L-DOPA). Early on in the disease, L-DOPA provides the chemical precursor to produce more of the waning domamine neurotransmitter, but gradually, there are fewer of these cells remaining that can benefit from such a boost in chemical processing. Furthermore, there are two side effects that patients find disturbing: 1) the symptoms that return during the wearing off phase after taking a dose, producing more radical on-off swings in motor symptoms, and 2) the gradual development of involuntary movements termed dyskinesias ["Levodopa in the treatment of parkinson's disease" (Schapira, A H V and Emre, M and Jenner, P and Poewe, W) (2009) *Eur J Neurol* 16(9):982-9]. Although drug therapy remains the first-line standard of treatment for patients with Parkinson's disease, the long-term medical side effects of phamacological therapy has kept the surgical device treatment options for pharmacologically intractable Parkinson's disease alive.

There are 3 surgical lesion targets in the brain that have been found to reduce the symptomatology of Parkinson's disease effectively: the ventral intermediate nucleus (VIM) of the thalamus, the internal segment of the globus pallidus (GPi), and the subthalamic nucleus (STN). Because patients with Parkinson's disease generally require treatment on both sides of the brain, the efficacy of single sided lesion treatment was often tempered by the complications of bilateral therapy. One never wants to lesion a brain symmetrically. So lesions can be administered asymmetrically. One also is hesitant to use too large a lesion at any one sitting, so there was a frequency of having to return to surgery to enlarge a lesion that was not effective enough. It is possible that there are other potential surgical or stimulation targets, such as portions of the cerebral cortex.

Parkinson's disease has become the disease most widely treated so far by deep brain stimulation (DBS) ["Translational principles of deep brain stimulation" (Kringelbach, Morten L and Jenkinson, Ned and Owen, Sarah L F and Aziz, Tipu Z) (2007) *Nat Rev Neurosci* 8(8):623-35]. DBS appeared to be effective when used bilaterally, without the symmetrical lesion complications. In 1997 the US Food and Drug Administration approved the use of deep brain stimulation in Parkinson's disease. Stimulation of the same targets that were lesioned produced palliative effects ["Surgical treatment of parkinson's disease" (Koller, W C and Pahwa, R and Lyons, K E and Albanese, A) (1999) *J Neurol Sci* 167(1):1-10]. VIM lesions and stimulation were well characterized to reduce tremor, but although tremor is a hallmark of the disease, it is not the most disabling symptom for most patients. To better deal with the bradykinesia and rigidity, stimulation of the GPi and STN became the preferred targets. Although STN is now the dominant DBS target, it is unclear whether GPi, with a less burdensome set of cognitive side effects, might be better for some patients ["Pallidal vs subthalamic nucleus deep brain stimulation in parkinson disease" (Anderson, Valerie C and Burchiel, Kim J and Hogarth, Penelope and Favre, Jacques and Hammerstad, John P) (2005) *Arch Neurol* 62(4): 554-60]. As our experience with DBS has progressed, a direct comparison of pharmacological versus deep brain stimulation (bilateral GPi or STN stimulation) for Parkinson's disease found DBS to have advantages in quality of life outcomes in comparison with phamacological therapy despite the risks inherent in surgical treatment ["A randomized trial of deep-brain stimulation for parkinson's disease" (Deuschl, Günther and Schade-Brittinger, Carmen and Krack, Paul and Volkmann, Jens and Schäfer, Helmut and Bötzel, Kai and Daniels, Christine and Deutschländer, Angela and Dillmann, Ulrich and Eisner, Wilhelm and Gruber, Doreen and Hamel, Wolfgang and Herzog, Jan and Hilker, Rüdiger and Klebe, Stephan and Kloss, Manja and Koy, Jan and Krause, Martin and Kupsch, Andreas and Lorenz, Delia and Lorenzl, Stefan and Mehdorn, H Maximilian and Moringlane, Jean Richard and Oertel, Wolfgang and Pinsker, Marcus O and Reichmann, Heinz and Reuss, Alexander and Schneider, Gerd-Helge and Schnitzler, Alfons and Steude, Ulrich and Sturm, Volker and Timmermann, Lars and Tronnier, Volker and Trottenberg, Thomas and Wojtecki, Lars and Wolf, Elisabeth and Poewe, Werner and Voges, Jürgen and German Parkinson Study Group, Neurostimulation Section) (2006) *N Engl J Med* 355 (9):896-908, "Bilateral deep brain stimulation vs best medical therapy for patients with advanced parkinson disease: a randomized controlled trial" (Weaver, Frances M and Follett, Kenneth and Stern, Matthew and Hur, Kwan and Harris, Crystal and Marks, Jr, William J and Rothlind, Johannes and Sagher, Oren and Reda, Domenic and Moy, Claudia S and Pahwa, Rajesh and Burchiel, Kim and Hogarth, Penelope and Lai, Eugene C and Duda, John E and Holloway, Kathryn and Samii, Ali and Horn, Stacy and Bronstein, Jeff and Stoner, Gatana and Heemskerk, Jill and Huang, Grant D and CSP 468 Study Group) (2009) *JAMA* 301(1):63-73]. Nevertheless, there remains interest in lesions, whose effectiveness versus pharmacological therapy has also been shown ["Randomized trial of pallidotomy versus medical therapy for parkinson's disease" (Vitek, Jerrold L and Bakay, Roy A E and Freeman, Alan and Evatt, Marian and Green, Joanne and McDonald, William and Haber, Michael and Barnhart, Huiman and Wahlay, Natalie and Triche, Shirley and Mewes, Klaus and Chockkan, Vijay and Zhang, Jian-Yu and DeLong, Mahlon R) (2003) *Ann Neurol* 53(5):558-69], and whose long-term medical management and costs are considerably less than for patients who require life-long maintenance of DBS systems ["Are complications less common in deep brain stimulation than in ablative procedures for movement disorders?" (Blomstedt, Patric and Hariz, Marwan I) (2006) *Stereotact Funct Neurosurg* 84(2-3):72-81]. An especially compelling study of bilateral subthalmotomy argues the rationale for lesions and demonstrates the apparent safety and risk assessment of symmetric subthalamic nucleus lesions ["Bilateral subthalamotomy in parkinson's disease: initial and long-term response" (Alvarez, L and Macias, R and Lopez, G and Alvarez, E and Pavon, N and Rodriguez-Oroz, M C and Juncos, J L and Maragoto, C and Guridi, J and Litvan, I and Tolosa, E S and Koller, W and Vitek, J and DeLong, M R and Obeso, J A) (2005) *Brain* 128(Pt 3):570-83].

The lesion debate notwithstanding, there is no more fruitful arena to consider a radical new approach to neural systems control than DBS technologies for Parkinson's disease. Our present approach has been to focus on high frequency stimulation (130 Hz) delivered in open loop without feedback sensing. suggesting the potential to incorporate feedback systems to improve our management of the symptoms of Parkinson's disease. There is impressive prior art [U.S. Pat. No. 2009/0018609 a1 (DiLorenzo), U.S. Pat. No. 7,266,412 b2 (Stypulkowski)] proposing a range of empirical feedback control strategies. An improvement over such empirical inventions is to use our increasingly sophisticated computational models of the fundamental networks involved in the pathophysiology of Parkinson's disease. The present invention extends this prior art to realms where one skilled in the field would not have previously been able work.

The Networks of Parkinson's Disease

A great deal of the brain, especially the regions beneath the cortex, is heavily involved with movement regulation. Such areas include the connected set of basal ganglia, portions of the thalamus, the cerebral neocortex, and the cerebellum.

In Parkinson's disease, there is degeneration of neurons that use dopamine as a neurotransmitter which have their cell bodies in the substantia nigra at the upper edge of the midbrain. The decrease in neural output from the substantia nigra causes a disturbance in the network balance of excitation and inhibition, as schematized in Figure FIG. 2. The result is a net increase in inhibition from GPi to thalamus (for a much more detailed discussion of the circuitry see "The basal ganglia in parkinson's disease: current concepts and unexplained observations" (Obeso, Jose A and Marin, Concepcio and Rodriguez-Oroz, C and Blesa, Javier and Benitez-Temiño, B and Mena-Segovia, Juan and Rodríguez, Manuel and Olanow, C Warren) (2008) *Ann Neurol* 64 Suppl 2:S30-46). But the lines and arrows in these static diagrams refer to average firing rate or activity and do not reflect the dynamics that is critical to understand what is happening. In Parkinson's disease the inhibition to the thalamus becomes phasic and oscillates.

If, in FIG. 1, you place a thin probe and burn a small hole in the GPi or STN, the symptoms of tremor, bradykinesia, and rigidity decrease. We have understood the improvement in symptoms from the schematic in that the excessive amount of inhibition streaming out of the GPi and into the thalamus will be decreased. If you instead place a thin electrode into these same structures, and stimulate at 130 Hz, you will get an almost identical decrease in the symptoms of tremor, bradykinesia, and rigidity.

The thalamus is a walnut sized structure in the center of the brain. We used to view it predominantly as a relay center for things such as sensory information. The thalamus has a variety of relay stations re-synapsing touch, vibration, sound, and visual information onto a fresh set of neurons coursing to their respective cortical targets (see schematic in "The thalamus as a monitor of motor outputs" (Guillery, R W and Sherman, S M) (2002) *Philos Trans R Soc Lond B Biol Sci* 357(1428): 1809-21). Cause substantial damage to the thalamus such as from a stroke, and the brain will lose consciousness Posner, J. B. and Plum, F. (2007) *Plum and Posner's diagnosis of stupor and coma* volume 71 Oxford University Press Oxford 4th ed edition. The concept of a cortex heavily interconnected with a series of relay loops to the deep thalamus has emerged, substantially complicating the older views "The thalamus as a monitor of motor outputs" (Guillery, R W and Sherman, S M) (2002) *Philos Trans R Soc Lond B Biol Sci* 357(1428): 1809-21.

Transmission within the cortex tends to be slow, with local conductance velocities in the range of centimeters per second, in contrast to the fast long range neural connections where many 10s of meters per second are commonly observed. We think that the thalamus forms an essential transcortical relay system to help integrate information processing across cortical areas where local conduction speeds would otherwise render us far dimmer.

It is the reliability of this relaying of motor information through the thalamus that will be a focus of the present invention. Nevertheless, one must ask why, if there is such an intimate relationship between cortex and thalamus, is so much of the medical treatment focusing on the lesioning or stimulation of targets many inches into the brain? Recent clinical trials have explored this issue, but so far, the results of these early efforts at superficial cortical stimulation have not been as effective as DBS or lesions "Therapeutic extradural cortical stimulation for parkinson's disease: report of six cases and review of the literature" (Gutiérrez, Julio C and Seijo, Fernando J and Alvarez Vega, Marco A and Fernández González, Fernando and Lozano Aragoneses, Beatriz and Blázquez, Marta) (2009) Clin Neurol Neurosurg 111(8):703-7.

Understanding the dynamics of Parkinson's disease was immeasurably helped by 1-methyl-4-phenyl-1,2,3,6-tetrahydropyridine (MPTP). It was discovered that this compound could produce Parkinsonian symptoms in non-human primates "A primate model of parkinsonism: selective destruction of dopaminergic neurons in the pars compacta of the substantia nigra by n-methyl-4-phenyl-1,2,3,6-tetrahydropyridine" (Burns, R S and Chiueh, C C and Markey, S P and Ebert, M H and Jacobowitz, D M and Kopin, I J) (1983) Proc Natl Acad Sci USA 80(14):4546-50. It was shown from both the human and animal data that MPTP was very selective in destroying the dopamine containing neurons in the pars compacta of the substantia nigra—the same sub-structure that prominently degenerated in human Parkinson's disease. The symptoms and signs of the drug-induced and natural disease were nearly identical, and both diseases responded to treatment with dopamine precursor drugs (L-DOPA). The full story of these events is remarkable [Langston, J. W. and Palfreman, J. (1995) The case of the frozen addicts Pantheon Books New York 1st ed edition, Factor, S. A. and Weiner, W. J. (2002) Parkinson's disease: diagnosis and clinical management Demos New York].

The critical benefits from these MPTP observations was the proof that loss of a small group of neurons in the substantia nigra could produce the triad of tremor, rigidity, and bradykinesia. The animal model provided us with a way to dramatically increase both our knowledge of the electrophysiology of the neuronal networks involved, and their potential electrical modulation, to the extent that the following invention can be described.

Prior to 2002, most models of Parkinson's disease were displayed as static diagrams (as in FIG. 2). Nevertheless, the advent of the MPTP primate model ["Pathophysiology of parkinson's disease: the mptp primate model of the human disorder" (Wichmann, Thomas and DeLong, Mahlon R) (2003) Ann NY Acad Sci 991:199-213, "Activity of pallidal and striatal tonically active neurons is correlated in mptp-treated monkeys but not in normal monkeys" (Raz, A and Frechter-Mazar, V and Feingold, A and Abeles, M and Vaadia, E and Bergman, H) (2001) J Neurosci 21(3):RC128], and increasingly the recording of neurons from human Parkinson's patients during deep brain surgery ["Single-unit analysis of the pallidum, thalamus and subthalamic nucleus in parkinsonian patients" (Magnin, M and Morel, A and Jeanmonod, D) (2000) Neuroscience 96(3):549-64, "Dopamine dependency of oscillations between subthalamic nucleus and pallidum in parkinson's disease" (Brown, P and Oliviero, A and Mazzone, P and Insola, A and Tonali, P and Di Lazzaro, V) (2001) J Neurosci 21(3):1033-8], revealed that the neurons within the Parkinsonian networks were strongly oscillatory (thalamus, GPi, and the external segment of the globus pallidus, GPe).

In the schematic of the basal ganglia, there are fundamental features of central pattern generators seen in the connectivity of GPe and STN. GPe cells inhibit each other as well as STN. STN excites GPe. When STN cells are inhibited, they also demonstrate an exaggerated rebound excitation ["Move to the rhythm: oscillations in the subthalamic nucleus-external globus pallidus network" (Bevan, Mark D and Magill, Peter J and Terman, David and Bolam, J Paul and Wilson, Charles J) (2002) Trends Neurosci 25(10):525-31]. Any simple neuronal membrane will spike if released suddenly from an inhibitory input—anode break excitation ["A quantitative description of membrane current and its application to conduction and excitation in nerve" (Hodgkin, A L and Huxley, A F) (1952d) J Physiol 117(4):500/11 Some of the neurons critical to Parkinsonian dynamics have additional currents that exaggerate such inhibition induced rebound excitation.

The rhythm generating circuitry shown in FIG. 2, turns out to also be the targets for both lesioning and stimulation in surgical therapy.

Three types of network topologies were constructed by ["Activity patterns in a model for the subthalamopallidal network of the basal ganglia" (Terman, D and Rubin, J E and Yew, A C and Wilson, C J) (2002) J Neurosci 22(7):2963-76]: random and sparsely connected, structured and sparsely connected, and structured and tightly connected. These are but examples of the types of network models that can be incorporated in model based control of Parkinson's disease.

To model the STN neurons, and bring out their rebound excitability, ["Activity patterns in a model for the subthalamopallidal network of the basal ganglia" (Terman, D and Rubin, J E and Yew, A C and Wilson, C J) (2002) J Neurosci 22(7):2963-76] model the STN membrane current as a combination of $$C_m \frac{dv}{dt} = I_L - I_K - I_{Na} - I_T - I_{Ca} - I_{AHP} - I_{G \to S} \quad (1)$$

where $C_m$ is membrane capacitance.

The first three currents ($I_L$-$I_K$-$I_{Na}$) are the Hodgkin-Huxley leak, rectifying potassium, and fast sodium which evolution elected to conserve from cephalopods to mammals ["A quantitative description of membrane current and its application to conduction and excitation in nerve" (Hodgkin, A L and Huxley, A F) (1952d) J Physiol 117(4):500-44]. In this case, these currents have parameters tailored to the mammalian neurons rather than the squid axon. $I_{G \to S}$ represents the current injected into these cells from the GPe synapses.

Additional currents can be added or subtracted as indicated in these fundamental models of neuronal physics. The after hyperpolarization current, $I_{AHP}$, is a potassium channel that opens in response to increasing amounts of intracellular calcium. While it is on, it prevents the cell from firing another spike, so it takes an important role in turning off excitation, as well as regulating firing frequency. It's a good way to create resonance frequency ranges within which a cell would prefer to fire. And it's a good way to generate a pacemaker. It is prominent in motoneurons in the spinal cord, where the frequency of discharge must be matched to the characteristics of the muscle fibers they connect to (fast or slow) ["Discharge properties of motoneurones: how are they matched to the properties and use of their muscle units?" (Kernell, D and Bakels, R and Copray, J C) (1999) *J Physiol Paris* 93(1-2): 87-96]. $I_{AHP}$ is prominent in the suprachiasmatic nucleus where it helps translate the molecular clock of our circadian rhythms into neuronal firing frequency ["After hyperpolarization regulates firing rate in neurons of the suprachiasmatic nucleus" (Cloues, Robin K and Sather, William A) (2003) *J Neurosci* 23(5):1593-604]. And $I_{AHP}$ is important in the subthalamic nucleus, helping to make the neurons more sensitive to inputs at motor frequencies, and helping to create an oscillatory central pattern generator out of the network it is embedded in the basal ganglia ["Move to the rhythm: oscillations in the subthalamic nucleus-external globus pallidus network" (Bevan, Mark D and Magill, Peter J and Terman, David and Bolam, J Paul and Wilson, Charles J) (2002) *Trends Neurosci* 25(10):525-31].

The high-threshold calcium current, $I_{Ca}$, is a representation of what are likely several high threshold calcium channels in such cells ["Characterization of ca(2+) channels in rat subthalamic nucleus neurons" (Song, W J and Baba, Y and Otsuka, T and Murakami, F) (2000) *J Neurophysiol* 84(5): 2630-7]. High threshold means that they are activated with depolarization. Because the calcium Nernst reversal potential is very positive (even more positive than sodium), these channels in general support regenerative potentials (that is they boost depolarization already in progress). Bursting cells tend to have such channels.

The low-threshold calcium current, $I_T$, is prominently seen in thalamic neurons where following inhibition such neurons rebound burst fire ["Sleep and arousal: thalamocortical mechanisms" (McCormick, D A and Bal, T) (1997) *Annu Rev Neurosci* 20:185-215]. This current activates upon hyperpolarization, and then deactivates more slowly than $I_{Na}$ deactivates as the neuron depolarizes. Since the reversal potential for calcium is positive, activating such a current gives the neuron a boost to bring its membrane potential away from rest and accentuate the tendency of any neuron to rebound a bit (as anode break excitation). $I_T$ plays a role in the prominent post-inhibitory rebound spiking seen in STN cells ["Move to the rhythm: oscillations in the subthalamic nucleus-external globus pallidus network" (Bevan, Mark D and Magill, Peter J and Terman, David and Bolam, J Paul and Wilson, Charles J) (2002) *Trends Neurosci* 25(10):525-31].

["Activity patterns in a model for the subthalamopallidal network of the basal ganglia" (Terman, D and Rubin, J E and Yew, A C and Wilson, C J) (2002) *J Neurosci* 22(7):2963-76] used the same currents as equation (1) for modeling GPe neurons, but changed their proportions so that they better matched the tiring properties seen in a variety of experimental studies. These proportions can be freely modulated to optimize the model tracking of the real Parkinson's diseased brain in this invention.

As pointed out by ["Activity patterns in a model for the subthalamopallidal network of the basal ganglia" (Terman, D and Rubin, J E and Yew, A C and Wilson, C J) (2002) *J Neurosci* 22(7):2963-76], the strength of connectivity (maximal synaptic conductance) can be varied from STN to GPe, and within the GPe to GPe network, to change the network model from normal to a Parkinsonian one. Increasing the STN to GPe coupling produced a range of behaviors from sparse irregular firing, to episodic bursting, to continuous firing. The episodic regime was qualitatively similar to that reported in the classic study by Delong for cells in the normal primate GPe ["Activity of pallidal neurons during movement" (DeLong, M R) (1971) *J Neurophysiol* 34(3):414-27]. One of the counterintuitive features of increasing the GPe to GPe inhibition is that it can increase the spread of activity through rebound firing. In the modeling of ["Activity patterns in a model for the subthalamopallidal network of the basal ganglia" (Terman, D and Rubin, J E and Yew, A C and Wilson, C J) (2002) *J Neurosci* 22(7):2963-76], the episodic burst firing is terminated by $I_{AHP}$ as calcium is built up in GPe cells during the high frequency firing episodes.

In a more tightly connected structured network one can wrap the model network around on itself (periodic boundary conditions). This network can generate waves that travel. Initiating such waves requires symmetry breaking in the STN-to-GPe and GPe-to-STN footprints. To form a solitary traveling wave, the GPe-to-GPe inhibitory footprint has to be larger spatially than the STN-to-GPe footprint (supporting a Turing instability [Murray, J. (2003) *Mathematical Biology: Spatial models and biomedical applications* Springer Verlag Berlin]). Key here is that for a wave to be propagated in the model, the STN and GPe cells have to have structured footprints so as to orderly spread activity to cells ahead of the leading edge of the wave ["Activity patterns in a model for the subthalamopallidal network of the basal ganglia" (Terman, D and Rubin, J E and Yew, A C and Wilson, C J) (2002) *J Neurosci* 22(7):2963-76].

Traveling waves have been experimentally observed in thalamic slices generating what are called spindle oscillations ["Spindle waves are propagating synchronized oscillations in the ferret lgnd in vitro" (Kim, U and Bal, T and McCormick, D A) (1995) *J Neurophysiol* 74(3):1301-23]. Spindle waves have been related to sleep physiology, but the relationship to Parkinson's disease is not presently clear. Nevertheless, whenever there is evidence of temporal oscillations in a neural network, it is worth considering what the spatial structure of those oscillations are ["Spiral waves in disinhibited mammalian neocortex" (Huang, X. and Troy, W. C. and Yang, Q. and Ma, H. and Laing, C. R. and Schiff, S. J. and Wu, J. Y.) (2004) *Journal of Neuroscience* 24(44):9897-9902]. Especially when networks are sparsely connected (as opposed to all-to-all connected where there is no meaningful spatial structure), considering whether waves might underlie such rhythms is a reasonable question, and should be taken into account in creating model-based control of this condition.

Strong oscillations emerge in the GPe-STN network in Parkinson's disease and in dopamine depletion in experimental animals. Nevertheless, there is a body of experimental evidence, in both human patients as well as MPTP primates (see ["Activity patterns in a model for the subthalamopallidal network of the basal ganglia" (Terman, D and Rubin, J E and Yew, A C and Wilson, C J) (2002) *J Neurosci* 22(7):2963-76]), that fails to find the sort of highly correlated and synchronized firing that would support the coherent waves predicted in the most structured networks. The picture emerging from this work is that among the more sparse networks, the conversion from normal to Parkinsonian dynamics fit well with the schematic in FIG. 2. Following a loss of dopamine input to the striatum, in the model one strengthens striatal input to the GPe, along with concurrent weakening of recurring inhibitory connections within the GPe, in order to model a Parkinsonian state.

In the standard firing rate model of Parkinson's disease FIG. 1, a decrease in inhibition to the striatum leads to an increased activity of STN, which increases excitation to GPe and GPi, which increases the inhibition to the thalamus. No oscillations arise in the static model, in a disease whose hallmark are the oscillations both within and outside the brain. The level of striatal input (inhibitory) is a major regulator of whether oscillations arise from within this network that is naturally wired and poised to oscillate. Increased striatal inhibition effectively strengthens the coupling from GPe to STN. Decreasing intra-GPe inhibition would promote clustered activity within GPe. And inhibition, as is found in other dynamic phenomena in the nervous system such as seizures, plays multifaceted and complex roles ["Interneuron and pyramidal cell interplay during in vitro seizure-like events" (Ziburkus, Jokubas and Cressman, John R and Barreto, Ernest and Schiff, Steven J) (2006) *J Neurophysiol* 95(6):3948-54, "The multifaceted role of inhibition in epilepsy: seizure-genesis through excessive gabaergic inhibition in autosomal dominant nocturnal frontal lobe epilepsy" (Mann, Edward O and Mody, Istvan) (2008) *Curr Opin Neurol* 21(2):155-60]. Inhibition in neuronal systems, similar to inhibitory reactants in reaction diffusion systems, is crucial in organizing patterns into clustered as opposed to homogeneous patterns [Murray, J. (2003) *Mathematical Biology: Spatial models and biomedical applications* Springer Verlag Berlin].

The Deep Brain Stimulation Paradox

Deep brain stimulation of the GPi or STN has almost identical effects on the symptoms of Parkinson's disease as do lesions of the GPi or STN. We have evidence of excessive activity of GPi in Parkinson's disease, but stimulation of STN should further increase GPi activity.

For several years it was therefore assumed that stimulation at the DBS frequencies being used (typically 130 Hz) must have been suppressing activity within the nuclei. This was supported by data showing that recording in the vicinity of the cell bodies within STN when stimulating STN ["Effect of high-frequency stimulation of the subthalamic nucleus on the neuronal activities of the substantia nigra pars reticulata and ventrolateral nucleus of the thalamus in the rat" (Benazzouz, A and Gao, D M and Ni, Z G and Piallat, B and Bouali-Benazzouz, R and Benabid, A L) (2000) *Neuroscience* 99(2):289-95], or recording within GPi with GPi stimulation ["High frequency stimulation of the internal globus pallidus (gpi) simultaneously improves parkinsonian symptoms and reduces the firing frequency of gpi neurons in the mptp-treated monkey" (Boraud, T and Bezard, E and Bioulac, B and Gross, C) (1996) *Neurosci Lett* 215(1):17-20], demonstrated a decrease in apparent cell firing following nearby high frequency stimulation. In computational modeling, McIntyre and colleagues ["Cellular effects of deep brain stimulation: model-based analysis of activation and inhibition" (McIntyre, C. C. and Grill, W. M. and Sherman, D. L. and Thakor, N. V.) (2004) *Journal of neurophysiology* 91(4):1457]demonstrated that such DBS stimulation close to cell bodies and axons might preferentially initiate action potentials further out along the axons of such neurons than we have appreciated previously, and furthermore that the cell bodies might not reflect these action potentials. Such findings also reminds one of the differing requirements in the curvature of a stimulating electrical field needed to initiate firing at the terminal end of a neuron process membrane, as opposed to the middle of a membrane such as an axon coursing near an electrode en passage ["Modeling the effects of electric fields on nerve fibers: determination of excitation thresholds" (Warman, E N and Grill, W M and Durand, D) (1992) *IEEE Trans Biomed Eng* 39(12):1244-54]. More recently, optical imaging has also confirmed that action potential initiation may be well beyond the axon hillock as we have previously assumed ["Effects of uniform extracellular dc electric fields on excitability in rat hippocampal slices in vitro" (Bikson, Marom and Inoue, Masashi and Akiyama, Hiroki and Deans, Jackie K and Fox, John E and Miyakawa, Hiroyoshi and Jefferys, John G R) (2004) *J Physiol* 557(Pt 1):175-90]. Helping to make further sense of this were the findings, in neurons different from the basal ganglia, that synaptic depression could occur at modest stimulation frequencies while the synapses ploddingly worked to repackage neurotransmitter within synaptic vesicles for release ["Presynaptic modulation of ca3 network activity" (Staley, K J and Longacher, M and Bains, J S and Yee, A) (1998) *Nat Neurosci* 1(3):201-9]. These findings were all consistent in explaining why DBS had the same effects as ablative lesions. This assumption was unfortunately wrong.

The definitive experimental evidence that laid to rest the hypothesis that DBS worked by suppressing neuronal activity and creating a reversible lesion was the demonstration that such stimulation led to an increase in firing frequency in the nucleus receiving the efferent activity from the nucleus being stimulated ["Stimulation of the subthalamic nucleus changes the firing pattern of pallidal neurons" (Hashimoto, Takao and Elder, Christopher M and Okun, Michael S and Patrick, Susan K and Vitek, Jerrold L) (2003) *J Neurosci* 23(5):1916-23].

So if increasing the frequency of GPi activity through stimulation of STN had the same effect as burning a hole in GPi, the reason had to lie in the dynamics of the effect of increasing the firing rate of GPi. Note 2 things about the effect of stimulation on GPi activity in ["Stimulation of the subthalamic nucleus changes the firing pattern of pallidal neurons" (Hashimoto, Takao and Elder, Christopher M and Okun, Michael S and Patrick, Susan K and Vitek, Jerrold L) (2003) *J Neurosci* 23(5):1916-23]: 1) the frequency is increased, and 2) the neural response becomes less episodic and more continuous. It is impossible to understand this set of findings from the raw data. The only way to explain this is with a computational model that reflects the fundamental biological processes. Similarly, there is no way to adequately observe this system without a fundamental computational model that was close to the real brain system. One can track natural processes with a poor model—you can use a constant model of weather and say that the weather in the next 60 seconds will be the same as it is now. But models are not predictive on time scales relevant to the dynamics, the changes in a complex system.

Observing a natural system requires a fundamental model with fidelity to that natural system. Observability is linked to reachability—that is, our ability to control a system (the states reachable with control) is intimately linked to the states we can observe and reconstruct with our fundamental model. This critical duality of reachability and observability is the key to the present invention, and what distinguishes it from all prior art. We will here rely on fundamental models to observe the Parkinson's disease brain, and use those observations to direct and regulate control.

Prior art such as [U.S. Pat. No. 2009/0018609 a1 (DiLorenzo), and U.S. Pat. No. 7,266,412 b2 (Stypulkowski)], never envisioned the importance of constructing fundamental models for both observation as well as control. Their models were empirical, based on the statistics or signal processing of data, without the benefit of what we understand about constructing fundamental models that have fidelity to the brain networks we seek to control.

Fitting empirical models to Parkinson's data might produce an effective controller, but would be no more insightful or predictive than proving that you could fit a model to prove that the neurons did what you had observed them to do up to the present. The power of model-based control approaches is that we take the insights from what we have learned about these pieces of brain we are working with, and use those fundamental models to guide our observations and control predictively.

The motor structures within the thalamus will be viewed as a structure whose task is to faithfully relay information. The thalamus will have 2 inputs: GPi and sensorimotor signals (FIG. 2).

"High frequency stimulation of the subthalamic nucleus eliminates pathological thalamic rhythmicity in a computational model" (Rubin, Jonathan E and Terman, David) (2004) *J Comput Neurosci* 16(3):211-35 distilled the essence of Parkinson's disease symptoms within the output of GPi. In the normal state these cells fire irregularly and do not interfere with thalamic information relay. In Parkinson's disease, GPi cells fire bursts of action potentials at the frequency of tremor (3-8 Hz). "High frequency stimulation of the subthalamic nucleus eliminates pathological thalamic rhythmicity in a computational model" (Rubin, Jonathan E and Terman, David) (2004) *J Comput Neurosci* 16(3):211-35 assumed that these burst firing cells will exhibit some degree of synchrony in the pathological state. Their hypothesis is that such clustered firing in bursts would impair the sensorimotor relay properties of the thalamic cells.

The sparse structured network from "Activity patterns in a model for the subthalamopallidal network of the basal ganglia" (Terman, D and Rubin, J E and Yew, A C and Wilson, C J) (2002) *J Neurosci* 22(7):2963-76 will be chosen, but any valid topology of the network connectivity can be used. Since there is uncertainty about the actual topology of real brain networks, selecting the topology for the model that gives the lowest tracking errors is a logical way to choose the connectivity in our model in this invention. Alternatively, running several candidate topologies in parallel is a powerful way to select the best performing candidate connectivity based on a winner take all competition between candidate topologies.

Thalamic cells can be modeled after "High frequency stimulation of the subthalamic nucleus eliminates pathological thalamic rhythmicity in a computational model" (Rubin, Jonathan E and Terman, David) (2004) *J Comput Neurosci* 16(3):211-35 with $$C_m \frac{dv_{Th}}{dt} = -I_L - I_{Na} - I_K - I_T - I_{Gi \to Th} + I_{SM} \quad (2)$$

where $I_{Gi \to Th}$ represents synaptic current from GPi to thalamus, and $I_{SM}$ represents sensorimotor input to thalamus. They are of opposite sign because one is inhibitory and the other excitatory.

The leak current is $$I_L = g_L \cdot (v_{Th} - E_L) \quad (3)$$

where $g_L$ is the maximal leak conductance, $v_{Th}$ is the transmembrane voltage on the thalamic cell, and $E_L$ is the reversal potential at which there would be no leak current when $v_{Th} = E_L$.

The sodium current is from Hodgkin and Huxley (Hodgkin:1952d)

$$I_{Na} = g_{Na} \cdot m_\infty^3(v_{Th}) \cdot h_{Th} \cdot (v_{Th} - E_{Na}) \quad (4)$$

except for the use of Rinzel's approximation "Excitation dynamics: insights from simplified membrane models" (Rinzel, J) (1985) *Fed Proc* 44(15): 2944-6, substituting $m_\infty$ for m in the sodium gating variable, and in the following potassium current equation, substituting $1 - h_{Th}$ for n for the potassium gating variable (h is the sodium inactivation gating variable)

$$I_K = g_K \cdot [0.75(1 - h_{Th})^4] \cdot (v_{Th} - E_K) \quad (5)$$

The T-type calcium current equation is $$I_T = g_T p_\infty^2(v_{Th}) \cdot w_{Th} \cdot (v_{Th} - E_T) \quad (6)$$

where $p_\infty(v_{Th})$ is the T-current gating variable, and $w_{Th}$ is the T-current inactivation variable. In these equations, the reversal potentials for leak, sodium, potassium, and T-current, are $E_L$, $E_{Na}$, $E_K$, and $E_T$, respectively.

The inactivation variables follow the Hodgkin-Huxley formalism for first order kinetics $$\frac{dh_{Th}}{dt} = (h_\infty(v_{Th}) - h_{Th}) / \tau_h(v_{Th}) \quad (7)$$

and $$\frac{dw_{Th}}{dt} = (w_\infty(v_{Th}) - w_{Th}) / \tau_w(v_{Th}) \quad (8)$$

The sensorimotor current, $I_{SM}$, was prescribed to be either periodic or at times random. The symmetry introduced in this equation by the canceling currents $-I_{Gi \to Th} + I_{SM}$ will cause us difficulties which we will address below, and a more complete discussion of symmetries in reconstruction can be found in ["Data assimilation for heterogeneous networks: the consensus set" (Sauer, Timothy D and Schiff, Steven J) (2009) *Phys Rev E Stat Nonlin Soft Matter Phys* 79(5 Pt 1):051909].

These thalamocortical (TC) cells are silent if unstimulated. If stimulated with depolarizing current, they fire progressively faster. However, if hyperpolarized, one sees progressively more and more intense rebound activity due to the T-current.

We can provide an analog to sensorimotor stimulation to this TC cell by periodically stimulating it. This is a signal that we hope the cell can relay. With slow stimulation the signal can be reliably relayed. If we now simultaneously provide the cell with excessive inhibition, such as in Parkinson's disease, from an overactive GPi, the baseline membrane potential is now more hyperpolarized. Now with each sensorimotor pulse, the cell rebound spikes because the T-current is deinactivated. This is because hyperpolarization removes $I_T$ inactivation, just as in the sodium inactivation in the Hodgkin-Huxley gating variable h. Removing inactivation is relatively slow. With higher stimulation frequencies, the TC cell is reliable, and it remains so in the setting of additional inhibition because there is insufficient time for the inactivation to deinactivate.

STN cells were modeled with $$C_m \frac{dv_{Sn}}{dt} = -I_L - I_{Na} - I_K - I_T - I_{Ca} - I_{AHP} - I_{Ge \to Sn} + I_{DBS} \quad (9)$$

Here "High frequency stimulation of the subthalamic nucleus eliminates pathological thalamic rhythmicity in a computational model" (Rubin, Jonathan E and Terman, David) (2004) *J Comput Neurosci* 16(3):211-35 added a high-threshold calcium current, $I_{Ca}$, and the synaptic current is now from GPe to STN, $I_{Ge \to Sn}$. There is also a deep brain stimulation current, $I_{DBS}$. The parameters on the STN cells were adjusted so that the cell was spontaneously active, fired at high frequencies when depolarized, and had a less prominent rebound than the TC cell. All of these adjustments were to preserve as much of the qualitative distinction between these cells' firing properties as observed in prior experiments.

GPe cells were modeled with $$C_m \frac{dv_{Ge}}{dt} = -I_L - I_{Na} - I_K - I_T - I_{Ca} - I_{AHP} - I_{Sn \to Ge} - I_{Ge \to Ge} + I_{app} \quad (10)$$

Input from the striatum was modeled with $I_{app}$. The GPe cells would continuously fire, initially decrease their firing rate with inhibition, and with more inhibition, cluster fire consistent with results in ["Activity patterns in a model for the subthalamopallidal network of the basal ganglia" (Terman, D and Rubin, J E and Yew, A C and Wilson, C J) (2002) *J Neurosci* 22(7):2963-76]. The GPi cells were similarly modeled, except the parameters were adjusted to account for the experimental evidence that these cells tended to fire faster than GPe cells ["Activity of pallidal neurons during movement" (DeLong, M R) (1971) *J Neurophysiol* 34(3):414-27]. Some further discussion about the applicability of ["Activity of pallidal neurons during movement" (DeLong, M R) (1971) *J Neurophysiol* 34(3):414-27] to the classification of human Parkinsonian cellular activity can be found in ["Neuronal spatiotemporal pattern discrimination: the dynamical evolution of seizures" (Schiff, Steven J and Sauer, Tim and Kumar, Rohit and Weinstein, Steven L (2005) *Neuroimage* 28(4): 1043-55].

Following the schematic in FIG. 2, the Parkinsonian state is recreated by increasing the striatal input to GPe, and decreasing the amount of internal recurrent inhibition within GPe. The result is that the normal reliability of the TC cell to transmit sensorimotor information, becomes impaired in the Parkinsonian state.

The key quantity here is the error rate of transmitting sensorimotor input into TC spikes. An error index can be created as $$\text{Error Index} = \frac{\text{missed spikes} + \text{bad spikes}}{\text{total inputs}}$$

$$= \frac{\text{false negative} + \text{false positive}}{\text{total inputs}}$$

Rubin and Terman "High frequency stimulation of the subthalamic nucleus eliminates pathological thalamic rhythmicity in a computational model" (Rubin, Jonathan E and Terman, David) (2004) *J Comput Neurosci* 16(3):211-35 showed that the error rate was significantly elevated in the Parkinsonian state in comparison with the normal state, and that the error rate could be normalized by simulating DBS using a constant level of high frequency stimulation of the STN. The key to understand these results is to know what the TC cell is receiving. In the Parkinsonian state, the amount of inhibition is fluctuating more than normal. This induces sequential excess suppression and rebound bursting in the TC cell which destroys reliability. By applying DBS, the fluctuations that the TC cell receives are decreased, despite an overall increase in GPi cell firing.

A key insight of ["High frequency stimulation of the subthalamic nucleus eliminates pathological thalamic rhythmicity in a computational model" (Rubin, Jonathan E and Terman, David) (2004) *J Comput Neurosci* 16(3):211-35] was that the qualitative features of the above could be preserved in the TC cell without the fast dynamics. This is only one example of a case where slow excitability dynamics may be more important than the faster spiking dynamics in determining pathological activities in dynamical disease. We have shown that in models of epileptic seizures, relatively slow fluctuations in potassium dynamics may underlie the more complex spike dynamics seen in individual cells ["The influence of sodium and potassium dynamics on excitability, seizures, and the stability of persistent states: I. single neuron dynamics" (Cressman, J. R. and Ullah, G. and Ziburkus, J. and Schiff, S. J. and Barreto, E.) (2009) *Journal of computational neuroscience* 26(2):159-170, "The influence of sodium and potassium dynamics on excitability, seizures, and the stability of persistent states: Ii. network and glial dynamics" (Ullah, G. and Cressman Jr, J. R. and Barreto, E. and Schiff, S. J.) (2009a) *Journal of Computational Neuroscience* 26(2): 171-183]. They take the TC membrane model and remove the fast Hodgkin-Huxley currents for sodium, $I_{Na}$, and potassium, $I_K$, and create a 2 variable description of TC cell membrane dynamics $$\frac{dv}{dt} = -(I_L + I_T)/C_{Th} - I_{Gi \to Th} + I_{SM} \quad (11)$$

$$\frac{dw}{dt} = \varphi \cdot (w_\infty(v) - w)/\tau_h(v)$$

In equations (11), v represents membrane voltage, φ serves as a relative rate constant between the two differential equations, w represents T-current inactivation, and the availability of T-current $I_T$ will be the key to reliability.

The current $I_{Gi \to Th}$ will be modeled as a true synaptic inhibitory input onto the TC cell as $$I_{Gi \to Th} = g_{Gi \to Th} \cdot s_{Gi} \cdot (v - E_{Gi \to Th}) \quad (12)$$

where $s_{Gi}$ will be a small positive constant in the normal, a periodic square wave in Parkinsonian, and a larger positive constant under conditions of DBS. But because there is a reversal potential attached to all synaptic ionic channels, $E_{Gi \to Th}$, the current $I_{Gi \to Th}$ will fluctuate with voltage v even when $s_{Gi}$ is a constant. The equations for the T-Current, $I_T$, are as given in equations (6) and (8).

The beauty of the 2-variable reduction of the TC cell is that the nullclines can be plotted in 2-dimensions and visualized. Nullclines are the curves where the rate of change of the variables are equal to zero. The intersection of more than one nullcline gives us the solutions, stable or unstable, of the system variables. Using nullclines is a simpler alternative system to fit were one interested in observing actual data, or developing control laws, than by using the full model.

In excitatory cells and their models, there is almost always a cubic or N-shaped nullcline for the fast excitatory variable, the voltage v in this case. Keep in mind that in this reduced model, there are no true action potential spikes (no $I_{Na}$ or $I_K$ currents). These phase space plots show us the slow dance between voltage changes, v, and $I_T$ inactivation, w. Increasing the synaptic current from GPi, $s_{Gi}$, as the DBS parameter in (12) literally adds the $I_{Gi \to Th}$ current term in (12) to the solution of the v nullcline. The reason is that when dv/dt=0, the solution of v is $$v = (I_L - I_{Gi \to Th} - I_{SM})/(g_{Ca} p_\infty (v - E_{Ca})) \quad (13)$$

where the very high positive reversal potential for calcium, $E_{Ca}$, always makes $(v - E_{Ca})$ negative. Because of the much more negative reversal potential $E_{Gi \to Th}$ for the inhibitory synapses, $(v - E_{Gi \to Th})$ is almost always positive. So the net effect is that increasing $I_{Gi \to Th}$ leads to an increase in the v nullcline as illustrated in FIG. 3A. This has a qualitatively opposite effect as increasing excitatory sensorimotor stimulation $I_{SM}$ in (11), which decreases the height of the v nullcline.

The point where these nullclines intersect is the resting steady state for v and for w. The T-current inactivation, w, is a key factor in whether this system will respond with a rebound burst, respond reliably to a sensorimotor input, or be inactive and unreliable by not responding at all.

When the intersection is brought lower on this phase plot, the system requires enough T-current, by having high enough w, to be able to push over the peak in the v̇ nullcline, the knee of this curve (the upgoing bump). As sensorimotor stimulus steadily increases, the value of w gradually decreases and the system is set up for trouble.

What this means is that if the position of the intersection of the nullclines is such that a stimulus ($I_{SM}$) comes when the value of w is above the knee of the v̇ nulcline, then the cell can fire a spike. If the system were subjected to episodic bursts of inhibition through a Parkinsonian GPi input to TC, then when the intense inhibition were released the cell would rebound. But hit the cell with an intense enough steady DBS input, the cell will maintain sufficient T-current and has no opportunity to rebound (there is no abrupt turn off of inhibition). Because in the Parkinsonian state the T-current availability fluctuates on and off, the result is tremor at this fluctuation frequency. DBS can level this out and simultaneously keep the cell in a state ready to fire reliably to excitatory inputs by keeping w moderately high.

Now let's look deeper into these reduced dynamics in normal, DBS, and Parkinsonian states. In FIG. 4 we see a normal state. The input to the reduced TC cell from the GPi is a modest constant, which represents a state where there is asynchrony among the GPi cells, and there results a modest steady level of inhibition to the TC cells. There is periodic sensorimotor stimulation represented by brief square wave excitatory inputs (second panel). A substantial amount of random measurement noise is added to the actual TC voltage. These noisy measurements are what we record from in these models as our observable variable. Note that for each sensorimotor stimulus, a 'spike' is transmitted from the TC cell. This is reliable transmission (100% reliable in this case).

The DBS state is modeled as increased tonic inhibition on the TC cell. The Parkinsonian case can be idealized as a periodic fluctuation in the GPi input onto the TC cells. In "High frequency stimulation of the subthalamic nucleus eliminates pathological thalamic rhythmicity in a computational model" (Rubin, Jonathan E and Terman, David) (2004) *J Comput Neurosci* 16(3):211-35, such an effect can be shown as a slow on and off square wave modulation of GPi output. Using the reduced model, when excess inhibition turns on, w gradually increases, T-current becomes more available, and spiking becomes more reliable after an initial suppression by the inhibition. When inhibition suddenly stops, w remains too high, and an excessive response with a period of rebound excitation occurs. During the trough of the Parkinsonian inhibition fluctuations, spikes are reliably transmitted but w gradually inactivates, and when the next inhibitory pulse hits, there is spike failure. This sequence of recurrent spike failure and rebound create unreliability. Since recall that in the reduced model there are no fast sodium spikes—the slow 'spikes' are periods of increased excitability; if we had $I_{Na}$ and $I_K$, we would get a burst of fast sodium spikes riding on the excitability rebound event and this would also reflect unreliable information transmission. Steady DBS, literally taking out the troughs in the Parkinsonian fluctuations, can restore reliability.

Feng and colleagues sought to further explore the work of Rubin and Terman by introducing optimization principles ["Optimal deep brain stimulation of the subthalamic nucleus—a computational study" (Feng, Xiao-Jiang and Shea-Brown, Eric and Greenwald, Brian and Kosut, Robert and Rabitz, Herschel) (2007a) *J Comput Neurosci* 23(3):265-82, "Toward closed-loop optimization of deep brain stimulation for parkinson's disease: concepts and lessons from a computational model" (Feng, Xiao-Jiang and Greenwald, Brian and Rabitz, Herschel and Shea-Brown, Eric and Kosut, Robert) (2007b) *J Neural Eng* 4(2):L14-21]. They, like ["High frequency stimulation of the subthalamic nucleus eliminates pathological thalamic rhythmicity in a computational model" (Rubin, Jonathan E and Terman, David) (2004) *J Comput Neurosci* 16(3):211-35], employed the sparse structured network of ["Activity patterns in a model for the subthalamopallidal network of the basal ganglia" (Terman, D and Rubin, J E and Yew, A C and Wilson, C J) (2002) *J Neurosci* 22(7):2963-76].

The disadvantage of using the same high frequency stimulation that presently demonstrates efficacy in clinical use is that the more energy applied per day the sooner the batteries of the stimulators wear out and the devices needs to be surgically replaced.

But beyond batteries, as stimulation intensities increase so will negative cognitive side effects ["Bilateral subthalamic stimulation impairs cognitive-motor performance in parkinson's disease patients" (Alberts, J. L. and Voelcker-Rehage, C. and Hallahan, K. and Vitek, M. and Bamzai, R. and Vitek, J. L.) (2008) *Brain* 131(12):3348]. All pulse stimulation of deep brain structures will have negative effects on cognitive information processing as stimulation is increased. This will likely apply to DBS treatment of cognitive disorders, such as depression and obsessive compulsive disorder, as well as to Parkinson's disease. In the treatment of any dynamical disease of the brain, one needs to optimize the beneficial effects of symptom relief (e.g. tremor), with the inherent effects of increasing cognitive dysfunction with increasing DBS energy.

In addition, it is not trivial to make clinical adjustments to a patient's stimulation parameters. Once set, the parameter space of stimulation intensity and frequency, along with duty cycle, is enormous. Making changes, waiting several days or weeks to see the steady state effect, and trying to optimize settings is difficult in patients. So if a stimulator is working and showing benefit, optimizing in this ad hoc fashion is generally avoided. Nevertheless, there is evidence that there are patients whose symptoms can be improved at frequencies different from the standard starting frequency of 130 Hz ["Stn-dbs frequency effects on freezing of gait in advanced parkinson disease" (Moreau, C and Defebvre, L and Destée, A and Bleuse, S and Clement, F and Blatt, J L and Krystkowiak, P and Devos, D) (2008) *Neurology* 71(2):80-4]. And more complex non-periodic stimuli delivered in open-loop might be more beneficial than the standard periodic ones.

Lastly, the beneficial effects of DBS over the long-term in a patient with a neurodegenerative disease (and perhaps those without degeneration) changes over time. Patients with DBS treatment of Parkinson's disease continue to deteriorate within the tempo of progression of Parkinson's disease ["Five-year follow-up of bilateral stimulation of the subthalamic nucleus in advanced parkinson's disease" (Krack, Paul and Batir, Alina and Van Blercom, Nadége and Chabardes, Stephan and Fraix, Valérie and Ardouin, Claire and Koudsie, Adnan and Limousin, Patricia Dowsey and Benazzouz, Abdelhamid and LeBas, Jean François and Benabid, Alim-Louis and Pollak, Pierre) (2003) *N Engl J Med* 349(20):1925-34]. Neural networks learn and change in response to stimulation. A means to automatically adapt and optimize such stimulation over time, such as the present invention, will be a very valuable advance in our stimulation technology.

One requires metrics for optimization. Feng and colleagues introduced a reliability measure similar to ["High frequency stimulation of the subthalamic nucleus eliminates pathological thalamic rhythmicity in a computational model" (Rubin, Jonathan E and Terman, David) (2004) *J Comput Neurosci* 16(3):211-35], as well as a GPi cell correlation metric. Neither metric has a clear route to practical application in human subjects using our present optimization done by hand. But these tools can be immediately applied if we construct a customized computational model for an average or specific patient. And this is the model-based approach that can be employed in automated closed-loop optimization as in the present invention.

The structure of Feng and colleagues' cost function was $$J^i = x^i + wR$$

$x^i$=criterion $i$(reliability or correlation)

$R$=energy required where w is a weighting parameter. They employed a genetic algorithm to search their parameter space and accomplish optimization.

One way of implementing such a cost function is to integrate the current coming out of the stimulator, $I_{DBS}$, and subtract this weighted integral from the reliability, Rel, as $$J = Rel - w \int_{t=0}^{T} I_{DBS} dt \qquad (14)$$

So starting from a sparse structured network, they then use their genetic algorithm to explore the parameter space of frequency and amplitude. In addition to the typical high-frequency and high-amplitude parameter regime typically employed in clinical use, where reliability is high, there are other reliable peaks. The most prominent additional peak is between 40-50 Hz, and indeed, there is some clinical evidence that this frequency range might be therapeutic ["Stn-dbs frequency effects on freezing of gait in advanced parkinson disease" (Moreau, C and Defebvre, L and Destée, A and Bleuse, S and Clement, F and Blatt, J L and Krystkowiak, P and Devos, D) (2008) *Neurology* 71(2):80-4]. Another exploration of frequency in an extended model demonstrated that the frequencies greater than 100 Hz were also effective ["A computational modelling approach to investigate different targets in deep brain stimulation for parkinson's disease" (Pirini, Marco and Rocchi, Laura and Sensi, Mariachiara and Chiari, Lorenzo) (2008) *Journal of Computational Neuroscience* 26:91-107].

There seems no way to directly measure in real life the quantities needed to calculate reliability: sensorimotor inputs and thalamic relay cell output in response to this input. But such inputs can be readily modeled and estimated using a data assimilation framework. Feng and colleagues ["Optimal deep brain stimulation of the subthalamic nucleus—a computational study" (Feng, Xiao-Jiang and Shea-Brown, Eric and Greenwald, Brian and Kosut, Robert and Rabitz, Herschel) (2007a) *J Comput Neurosci* 23(3):265-82] also employ a correlation measure, which was a combination of autocorrelation and crosscorrelation among GPi cells. This would require a microelectrode array to be placed within GPi. Such microarray technology is now becoming available on the shafts of clinical DBS electrodes. A simpler way to infer such correlation in practice would be to estimate spectral concentration in GPi local field potentials, and this is directly observable from an ordinary DBS electrode placed within GPi. One can use the computational model of this invention to reconstruct the autocorrelations and crosscorrelations that are not directly observable within nuclei such as GPi, GPe, STN, or the Thalamus.

An important contribution of ["Optimal deep brain stimulation of the subthalamic nucleus—a computational study" (Feng, Xiao-Jiang and Shea-Brown, Eric and Greenwald, Brian and Kosut, Robert and Rabitz, Herschel) (2007a) *J Comput Neurosci* 23(3):265-82] is that they demonstrated in this computational model that both stochastic stimulation, as well as complex waveforms, can demonstrate potential efficacy.

Guo and colleagues ["Thalamocortical relay fidelity varies across subthalamic nucleus deep brain stimulation protocols in a data-driven computational model" (Guo, Yixin and Rubin, Jonathan E and McIntyre, Cameron C and Vitek, Jerrold L and Terman, David) (2008) *J Neurophysiol* 99(3): 1477-92] took recordings of GPi spike timings from normal and MPTP primates, with and without DBS. They applied a structure function to these spike timings to re-create an estimate of the synaptic currents produced in the thalamic relay cells from such spiking. They used the model from ["High frequency stimulation of the subthalamic nucleus eliminates pathological thalamic rhythmicity in a computational model" (Rubin, Jonathan E and Terman, David) (2004) *J Comput Neurosci* 16(3):211-35] to estimate the reliability of the transmission of spikes through the thalamus. Their results demonstrate that the error index (described above) is higher for the MPTP monkeys without DBS or with subtherapeutic DBS, and consistently lowest for normal monkeys and those MPTP monkeys with therapeutic levels of DBS.

Using the reconstructed firing rates, autocorrelations, and crosscorrelation of cells within GPI as mentioned above, one can then use the computational model of this invention to estimate ongoing reliability, and perform closed-loop optimization.

A very interesting insight from ["Thalamocortical relay fidelity varies across subthalamic nucleus deep brain stimulation protocols in a data-driven computational model" (Guo, Yixin and Rubin, Jonathan E and McIntyre, Cameron C and Vitek, Jerrold L and Terman, David) (2008) *J Neurophysiol* 99(3):1477-92] was to reverse correlate what the inhibitory current drive from GPi was prior to a spike. Spikes can be faithful in following a sensorimotor input, can miss their chance to follow, or multiple bad spikes can ensue. Guo and colleagues found that missed spikes correspond to a relatively rapid rise in inhibition, and bad spikes correspond to a relatively rapid decrease in inhibition. This is exactly what one might have expected from the reduced model effects illustrated in FIG. 4.

We anticipate that Parkinson's disease will be the first dynamical disease amenable to management through model-based feedback control systems.

First, examine the schematic in FIG. 1. We can now relatively safely place electrodes in STN, GPi, or thalamus. There are small lesions created in placing electrodes into these deep brain targets. Yet in Parkinson's disease, making a lesion in these small structures is clinically beneficial. Amazingly, we observe that in the course of placing DBS electrodes in Parkinson's disease patients, there is an immediate clinical improvement in about half of patients at the conclusion of electrode placement, before the electrode is connected to the stimulator ["Deep brain stimulation is preferable to thalamotomy for tremor suppression" (Tasker, R R) (1998) *Surg Neurol* 49(2):145-53; discussion 153-4]. This has been termed the micro-thalamotomy effect. A nearly identical experience has been reported in the placement of deep brain stimulator electrodes in small thalamic targets for epileptic seizure suppression ["Chronic anterior thalamus stimulation for intractable epilepsy" (Hodaie, Mojgan and Wennberg, Richard A and Dostrovsky, Jonathan O and Lozano, Andres M) (2002) *Epilepsia* 43(6):603-8]. DBS treatments are a combination of small lesions overlain with chronic electrical stimulations.

Despite the beneficial effect of some of the microlesions created by electrode insertion, best clinical strategy is almost certainly to keep the number of electrodes inserted to the absolute minimum. From a surgical standpoint, every electrode insertion increases operative time, increases the risk of hemorrhage and neurological deficit, and increases the risk of infection. Surgical minimalism is a guiding principle in this present invention. But the network that is important in Parkinson's disease control is spread out over at least 4 separate structures: STN, GPe, GPi, and thalamus. Without model-based control, one might need to place electrodes into multiple structures in order to have an accurate measurement of the network activity requiring control.

From a clinical perspective, the GPi is an easier and safer target than the smaller STN or thalamic targets. A small hemorrhage or lesion effect in GPi has a reasonable chance of actually benefitting some of the Parkinson's disease symptoms.

The models we have just discussed permit us to sample from a single nucleus within this network and reconstruct what the remainder of the network is doing. Our present state of the art models appear sophisticated enough to consider using these models in a data assimilation framework. And the technology to perform chronic real-time sampling from these structures is presently available and in clinical use.

The first issue with parameter estimation for equation (11) is to notice that there is a symmetry with the terms $(-I_{Gi \to Th} + I_{SM})$. The tracking algorithm will simply apportion such current equally between these two sources. One option is to combine the currents into one sum which physically is what is happening to the TC cells. But this defeats our purpose here, where we would like to estimate quantities such as $(-I_{Gi \to Th})$ in isolation. A more extensive discussion of symmetries in such equations can be found in ["Data assimilation for heterogeneous networks: the consensus set" (Sauer, Timothy D and Schiff, Steven J) (2009) *Phys Rev E Stat Nonlin Soft Matter Phys* 79(5 Pt 1):051909].

When faced with such symmetries it is best to get rid of them "Data assimilation for heterogeneous networks: the consensus set" (Sauer, Timothy D and Schiff, Steven J) (2009) *Phys Rev E Stat Nonlin Soft Matter Phys* 79(5 Pt 1):051909. If that is not feasible, then an empirical rule of thumb seems to be to set process noise in rough proportions to the average magnitudes of the corresponding variables. One could adaptively tune these process noises over time by tracking innovation error. Innovation errors are the differences between what your model predicts you should observe in the next measurement, and what is actually measured. Process noise, Q, is uncertainty commonly added to the model of the process or plant in such applications. In this particular instantiation of ensemble Kalman filtering, we will use several Q values as the assumed variance in the respective parameters to be tracked. In addition to apportioning variance to the respective parameters, this also has the benefit of preventing a Kalman filter from driving the parameter covariance to zero. A detailed discussion of process noise can be found in [Simon, D. (2006) *Optimal state estimation: Kalman, H and nonlinear approaches* Wiley-Interscience Hoboken, N.J.]. In FIG. 5A, the Q for $(-I_{Gi \to Th})$ is 30, while the Q for $I_{SM}$ is 0.01. Note that the rhythmicity of $(-I_{Gi \to Th})$ is resolved, while none of the features of $I_{SM}$ are picked up. Now reverse the situation, setting Q for $(-I_{Gi \to Th})$ to 0.01 and the Q for $I_{SM}$ to 30; the $(-I_{Gi \to Th})$ will be poorly tracked, but the sensorimotor inputs $I_{SM}$ are better tracked as shown in FIG. 5B. A more optimized apportionment of process noise is shown in FIG. 5C.

We can calculate a running reliability index over the past 10 milliseconds (ignoring for now having to objectively define 'bad' spikes unrelated to sensorimotor inputs) as $$\text{Reliability} = \frac{\text{Number of spikes that got through (within 10 ms)}}{\text{Total number of impulses}}$$

Let's now focus on the heart of the dynamics critical for the Parkinsonian state—the T-current inactivation w. This is a rather independent variable, in time scale and with respect to symmetry, and lies at the heart of the issues of unreliability.

In Figure FIG. 6A, I employ the reduced TC cell model from in a data assimilation framework. The observable will be noisy voltage recorded from the TC cell in the upper panel of the figure. Below that is shown the reconstructed estimated T-current inactivation, w, and the reconstruction of estimated GPi and sensorimotor activity (panels 2-4 respectively). The principles of the techniques used to accomplish this reconstruction are detailed in ["Kalman filter control of a model of spatiotemporal cortical dynamics" (Schiff, Steven J and Sauer, Tim) (2008) *J Neural Eng* 5(1):1-8, "Data assimilation for heterogeneous networks: the consensus set" (Sauer, Timothy D and Schiff, Steven J) (2009) *Phys Rev E Stat Nonlin Soft Matter Phys* 79(5 Pt 1):051909, "Tracking and control of neuronal hodgkin-huxley dynamics" (Ullah, G. and Schiff, S. J.) (2009b) *Physical Review* E79(4):40901].

One could similarly record the average GPi output from a DBS electrode and reconstruct the estimated TC cell activity.

The sensorimotor input, in the 4th panel of Figure FIG. 6, causes the model TC cell to generate or fail to generate reliable spike activity in the upper panel. I build up a reliability index by averaging the last 10 sensorimotor spike responses, and plot this at the very top of the upper panel.

We next consider control from the nullclines. There is an extensive literature in control theory on what is generally termed variable structure control. First described by Utkin in the 1970s ["Variable structure systems with sliding modes" (Utkin, V.) (1977) *IEEE Transactions on Automatic control* 22(2):212-222], this control law strategy is now more commonly referred to as sliding mode control ["Variable structure control of nonlinear multivariable systems: a tutorial" (DeCarlo, R A and Zak, S H and Matthews, G P) (1988) *Proceedings of the IEEE* 76(3):212-232, "A control engineer's guide to sliding mode control. control systems technology" (Young, K. D. and Utkin, V I and Ozguner, A.) (1999) *IEEE Transactions on* 7(3):328-342]. We could use such nullclines to generate control functions that we seek to target the system towards. In FIG. 3A, we see the actual nullcline intersection of our simulation of the reduced TC cell as the GPi current switches from off to on. The w nullcline does not change as GPi input fluctuates. In FIG. 3B, I show an estimation of these nullclines from a reconstruction of these curves using an unscented Kalman filter.

As a substitute for the nullcline intersection, the value of w is a valuable single feature that helps account for the dynamical response of the TC cell. In the second panel of FIG. 6A is the estimate of the reconstructed T-current availability w. Note that w increases when the GPi current increases in the third panel. I have deliberately adjusted the ratios of the process noises so that the sensorimotor input is not tracked well (4th panel), in order to minimize the symmetry of this current in the voltage equation. In the bottom panel is shown the running plot of control energy, which is zero for this example without feedback.

Now let's use perfect deep brain stimulation. We will fill in the gaps of the fluctuating synaptic current from GPi, and show these results in FIG. 6B. Providing a steady level of DBS increases the amount of inhibition arriving on the TC cell. This has the effect of removing the fluctuations in inhibition creating the gaps in reliability shown in FIG. 6A, but it also dampens down the responsiveness of the TC cell. Only about half of the incident sensorimotor spikes get reliably through. And the cost in terms of control energy is high (8000 on an arbitrary scale). On the other hand, the fluctuations in w are reduced, and we maintain an overall high level of w (second panel FIG. 6B).

Now let's use adaptive feedback based upon the estimated w. In FIG. 7A, I show the effect of an optimal amount of proportional feedback gain based on a moving average (35 ms) of the estimate of w. This feedback is very effective in restoring most of the unreliable (missing) spikes. The total cost in control energy is about half of the perfect DBS case shown in FIG. 6B. Now let's present a more realistic DBS scenario than in Figure FIG. 6B, one in which a constant stimulation (open loop) will be added to the fluctuating Parkinsonian GPi signal. In FIG. 7B is shown the largest (and most effective) additive current that is stable in this model. We are here limited by the relatively large peak fluctuating GPi currents being applied already in the Parkinsonian state, as the dynamics of the TC cell become unstable if the impinging currents become excessive. The figure shows that such constant DBS does not appear capable of achieving the reliability possible with feedback control. In real implimentations in patients, such model instability would not arise. So long as we stay within the safety limit of the electrical stimulation, we might be able to deliver more GPi current to the TC cell. But the reliability steadily decreases in this scenario as this type of additive DBS increases in the model, since too much inhibition shuts off the TC cells. We find no inference that such open loop stimulation is going to be as effective as an intelligent adaptive approach as illustrated in FIG. 7A.

It is important to note that in this simple scenario, that there are a range of additional adjustable parameters that are important. First, there is the ever present issue of covariance inflation ["A Monte Carlo implementation of the nonlinear filtering problem to produce ensemble assimilations and forecasts" (Anderson, J. L. and Anderson, S. L.) (1999) *Monthly Weather Review* 127(12): 2741-2758]. In many of recursive filter designs, there is a trade-off between tracking accuracy versus stability with greater uncertainty. One also needs to counter the tendency of these filters to recursively drive the uncertainty to zero, which ruins tracking ability. In FIG. 8A, we see that adjusting the small covariance inflation parameter has a substantial effect on the reliability of the adaptive system. Similarly, the gain on the feedback control is important. In FIG. 8B, we see that optimizing gain readily reveals a region where spike throughput is best. Both of these functions are not smooth, and implementing such an algorithm should be done with continual adaptation of such parameters based upon the monitoring of the system performance through, for instance, innovation error.

Another alternative is to generate a control signal based upon the estimated GPi output, shown in Figure FIG. 9. Since we know the control signal added, we can subtract this to follow just the underlying estimated GPi input to the thalamus. Since the estimates of GPi input to thalamus are noisy (dotted line in FIG. 9), it is helpful to create a moving average filter of this estimate (solid line) to prevent the controller from turning on and off too often. Since at the heart of Parkinson's disease physiology are the large scale slower fluctuations, we can create a long-term running average of the GPi output, much longer than the noise reducing short-term moving average, and let this serve as an adapting threshold (solid line). Control is turned on whenever the short-term moving average falls below the long-term moving average. The control is applied in this case by turning on the stimulator with the same constant amplitude, shown as the horizontal lines. The underlying true GPi output fluctuations are shown as a black line for comparison. Note that a control reliability can be calculated as the fraction of time that the control signal is on or off in correct reflection of the peaks and valleys in the true GPi signal. In this example, the control reliability is 67%.

Reliability can be used as a control parameter. In FIG. 10A I show a control law that turns stimulation on when estimated reliability is too low.

To improve these results, recognize that what is delayed for the past is predictive of the future. If we use low reliability as a control variable, by the time the moving average of reliability decreases to an arbitrary threshold, turning on stimulation may come too late. But for periodic fluctuations, for which Parkinson's disease abounds, we can invert the control variable. This uses high reliability as a control threshold. By the time reliability becomes high enough, the lack of inhibition will be drawing to a close, and the incipient upturn in inhibition will be imminent. Such results can be useful, as shown in the improved control in FIG. 10B.

The calculations in Figures FIG. 3-FIG. 10 assumed that there are two electrodes inserted—a recording electrode in thalamus and a stimulating electrode in GPi or STN. The ideal Parkinson's controller would work off of a single electrode, albeit one with multiple contacts, inserted into just one nucleus. We can employ separate contacts for recording and stimulation along the electrode shaft. Perhaps picking up the oscillatory rhythms from GPi or STN would be sufficient for feedback control of those same nuclei. On the other hand, the models presented here give us the freedom to take such oscillatory dynamics from GPi or STN and estimate the reliability of the thalamus. We will not ever likely be able to record a good estimate of sensorimotor input to the actual thalamus, but we can provide such signals, or a range of such signals, to a model thalamus that is functioning with our observer model system when only GPi or STN serves as the recording site.

The reduced model of the TC cell is valuable for gaining intuition. Adding back the fast Hodgkin-Huxley sodium and potassium currents may be helpful in using such a model to track the thalamic dynamics, as might using an ensemble of such cells. But one of the appeals of such reduced models is that they can represent ensemble activity. Using a scaled up version of this reduced TC cell, renormalized to represent an ensemble of such cells, is an effective way to track thalamic dynamics in real brains.

Recent work has extended the models of ["High frequency stimulation of the subthalamic nucleus eliminates pathological thalamic rhythmicity in a computational model" (Rubin, Jonathan E and Terman, David) (2004) *J Comput Neurosci* 16(3):211-35] to take into account more biologically relevant connections, the direct versus indirect pathways from striatum to the structures of the basal ganglia ["A computational modelling approach to investigate different targets in deep brain stimulation for parkinson's disease" (Pirini, Marco and Rocchi, Laura and Sensi, Mariachiara and Chiari, Lorenzo) (2008) *Journal of Computational Neuroscience* 26:91-107]. The further incorporation of relevant model components may well give greater fidelity to the realistic basal ganglia dynamics in Parkinson's disease. But with our goal being control, such fidelity through complexity will need to be balanced against accuracy of data assimilation and control metrics. One of the important issues raised in "A computational modelling approach to investigate different targets in deep brain stimulation for parkinson's disease" (Pirini, Marco and Rocchi, Laura and Sensi, Mariachiara and Chiari, Lorenzo) (2008) *Journal of Computational Neuroscience* 26:91-107 is that a more complex model of the thalamic cell's function, beyond the simple relay, is likely important. One example of this is action selection theory, which envisions that the basal ganglia serves to select from competing neuronal efforts for access to the final common path of motor movement ["A physiologically plausible model of action selection and oscillatory activity in the basal ganglia" (Humphries, Mark D. and Stewart, Robert D. and Gurney, Kevin N.) (2006) *Journal of Neuroscience* 26:12921-12942]. Furthermore, as in human patient experience, the DBS target sites are not equivalent. Indeed, maintaining the flexibility to perform model-based control off of STN, GPi, thalamus, or even cortex, depending upon a patient's symptom complex, needs to be considered as options.

DESCRIPTION OF RELATED ART

Several devices have been proposed to better deal with dynamical diseases such as Parkinson's disease.

U.S. Pat. No. 7,266,412 b2 (Stypulkowski) discloses the generation of multiple neurostimulation therapy programs. Such programs are control laws for open loop (without feedback) stimulation devices. Such multiple programs are empirical stimulation schemes (pulse or non-pulse) that are activated, for instance, when a person is awake or is asleep. U.S. Pat. No. 7,266,412 b2 (Stypulkowski) does not disclose the use of fundamental models of the parts of the brain involved, nor does it discuss feedback modulation of the brain. Although we here discuss the use of parallel models, which may represent stages of vigilance such as awake or various sleep stages, these models actually represent the dynamics of the parts of the brain in question during those states of wakefulness. The parallel models of our invention are selected by which model synchronizes best to the brain being sensed, and generates the smallest tracking error among other possible models. The model selected is used because it in fact best represents and emulates the patient's brain for the time it is selected. One well versed in the art of U.S. Pat. No. 7,266,412 b2 (Stypulkowski) would not be able to accomplish what is disclosed in the present invention.

U.S. Pat. No. 2009/0018609 a1 (DiLorenzo) discloses in a patent application publication closed-loop feedback-driven modulation of the brain.

U.S. Pat. No. 2009/0018609 a1 (DiLorenzo) mentions use of a filter such as a Kalman filter to calculate parameters based upon a weighted combination of the sensory feedback signals. There is no description of the use of fundamental models, nor the lack of utility of the ordinary linear Kalman filter for such complex nonlinear models. In our present invention, we can only incorporate the complex nonlinear fundamental models using filtering specifically designed for such nonlinear systems, such as the ensemble Kalman filter, unscented Kalman filter, and variations of particle filtering appropriate for such fundamental models.

U.S. Pat. No. 2009/0018609 a1 (DiLorenzo) describes the use of an observer system to reconstruct unobserved variables, and discusses the inputs to the observer being the same control law output signals delivered to the controlled system. They further disclose the use of a model-based control law, wherein a computer-based dynamic model of the system being controlled is continuously adjusted according to a function of the difference between the model state and the measured state, and whereby the state of the model is then used to determine the control signal fed to the actual controlled system.

Yet nowhere in U.S. Pat. No. 2009/0018609 a1 (DiLorenzo) are any of the essential details provided to develop a fundamental model of the brain suitable for such model-based control, nor the necessary aspects of the filter required to function to assimilate data and reconstruct the dynamics of such a model. There is no mention of the fundamental models of relevant neuronal types, no discussion of ionic currents, no necessity to consider ion flow in the extracellular space, glia, and vasculature, there is no discussion of network topology, no discussion of the necessity to reduce such models to their fundamental physics, no discussion of the role of noise injected into the models to improve their observability and tracking, no discussion of model inadequacy and parametrization of inadequacy, no discussion of consensus sets, no discussion of covariance inflation, no discussion of synchronization between model and brain, no discussion of required initial conditions, no discussion of the need to eliminate symmetries from the fundamental model in order to achieve reliable and accurate tracking, no discussion of running fundamental models in parallel, no discussion of the necessity to admit non-physical and non-biological parameter values to optimize tracking in imperfect and reduced biological models, no discussion of using an observer model as a filter to remove real noise effects and measurement error from the parts of the brain being observed, and no discussion of the use of a health observer model to synchronize to and correct the dynamics of a diseased brain. One well versed in the art of U.S. Pat. No. 2009/0018609 a1 (DiLorenzo) would not be able to accomplish what is disclosed in the present invention.

Reliability is tracked as piecewise linear plot at very top. Process noise parameters are in A) Q1=0.001, Q2=30, Q3=0.01, in B) Q1=0.01, Q2=0.01, Q3=30, and in C) Q1=0.01, Q2=10, Q3=0.01.

Figure 6:
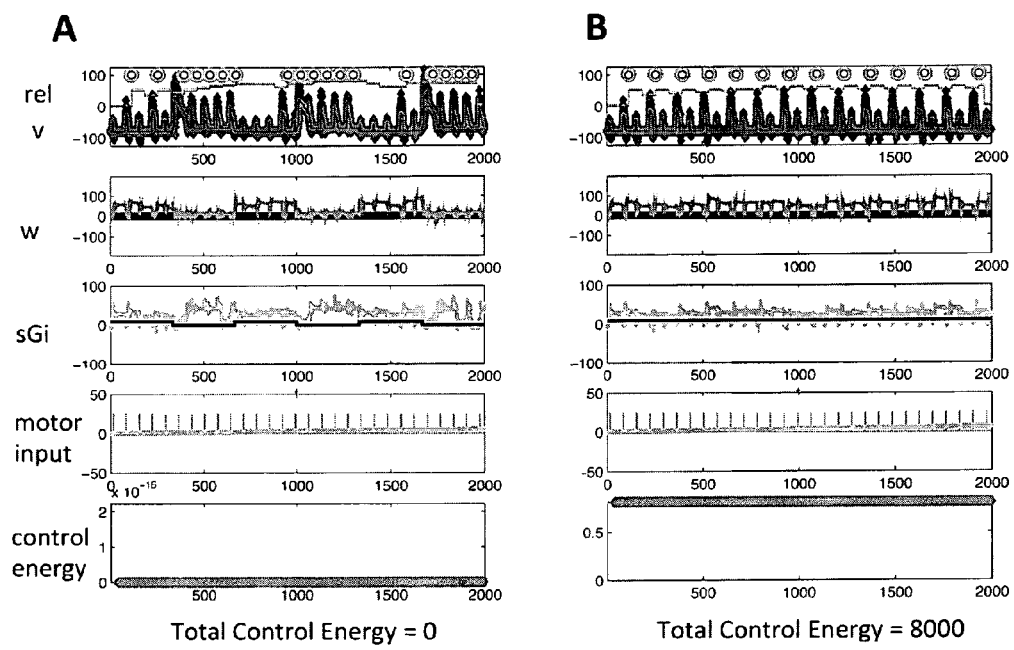

FIG. 6 shows an example of uncontrolled reduced TC cell dynamics in the Parkinsonian state with fluctuating current from GPi (sGi). B, perfect DBS stimulation filling in the troughs in the fluctuating current from GPi. Top panels show noisy observable voltage (markers), reliability as piecewise continuous plots, the circles are the timing of SM spikes, and the smaller circles contained within them are transmitted spikes. The second panels show estimated w. The third panels show real and estimated synaptic current from GPi (sGi, estimated values multiplied by 10 for discriminability from the true values). The fourth panel shows real and estimated motor input (we are deliberately not trying to reconstruct motor input in the reconstruction through Q ratio adjustment). The bottom panel shows the running control energy, the squared value of the control signal at each time point, and the total sum of squares given as total control energy.

Figure 7:
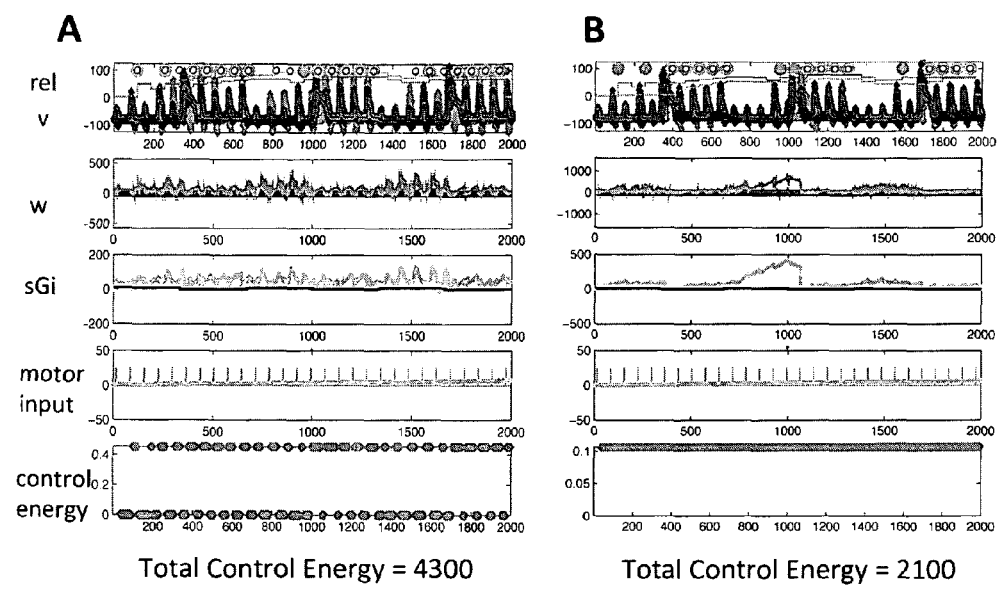

FIG. 7 shows an example of feedback control scenario based on turning on and off deep brain stimulator based on a running average of the estimated T-current availability shown in A. In B, we show a scenario where a constant amount of deep brain stimulation is simply added to the fluctuating Parkinsonian GPi output. No adjustment of GPi constant stimulation comes close to the reliability achieved with the closed loop feedback scenario shown in A. Symbols and lines as in FIG. 6

Figure 8:
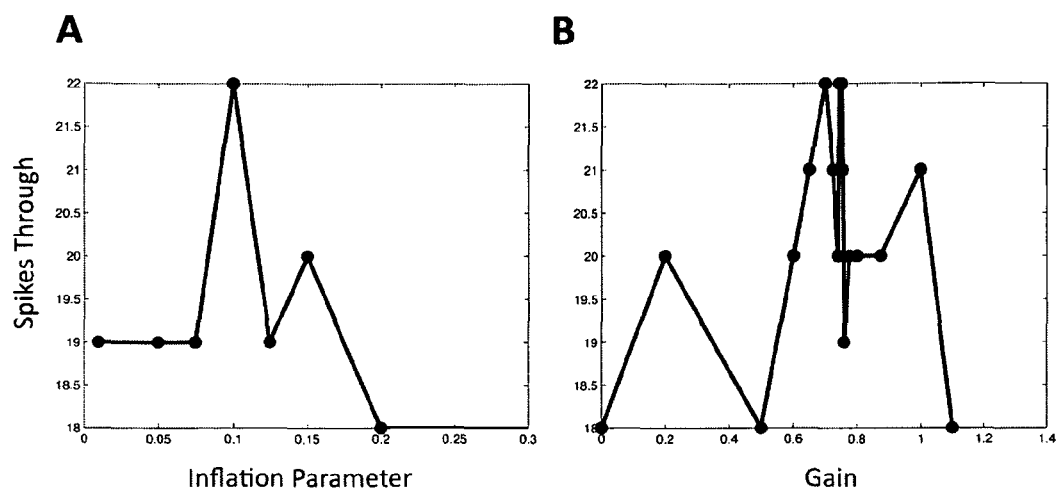

FIG. 8 shows an example of optimizing reliability as spikes that are transmitted reliably through the TC cell as a function of the covariance inflation parameter, A, and proportional control gain parameter, B.

Figure 9:
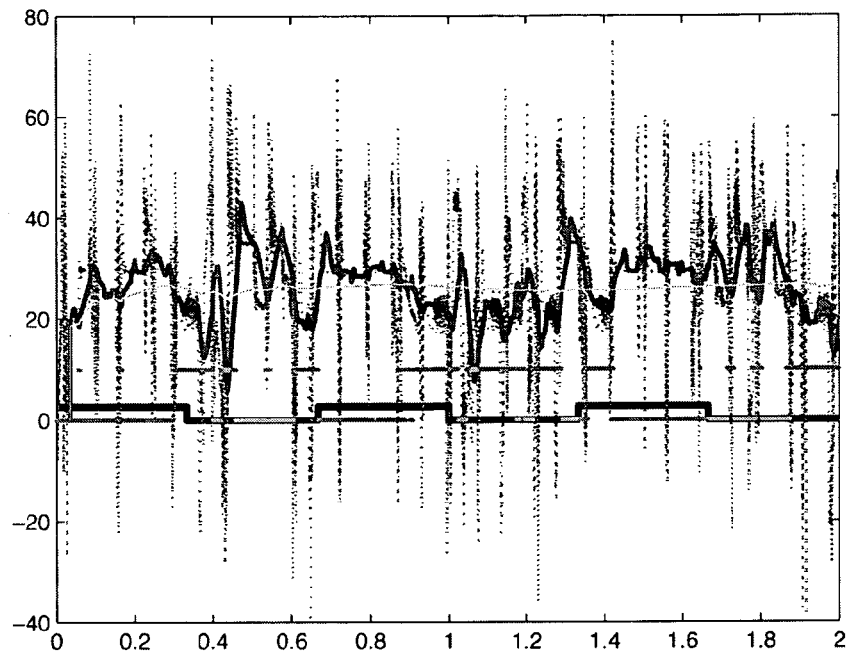
Figure 9:
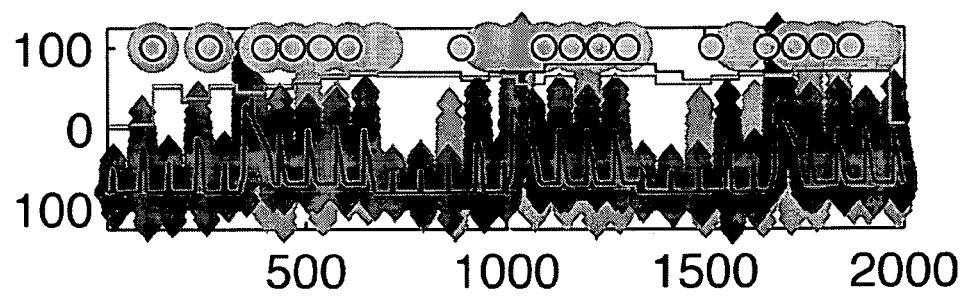

FIG. 9 shows an estimate of GPi input to TC cell (dotted line), and smoothed short-term moving average of this GPi input (solid line). We take a long-term moving average of this current (solid line) as an adapting threshold to tell when the more instantaneous GPi input is fluctuating up or down. Crossing below the threshold determines when to turn the control on. The actual GPi fluctuations are shown as horizontal lines. In the lower panel are the results with control off and on (markers), and the uncontrolled and controlled spikes (circles) transmitted. The running reliability of the TC cell is plotted as a piecewise continuous line for uncontrolled and controlled scenarios.

Figure 10:
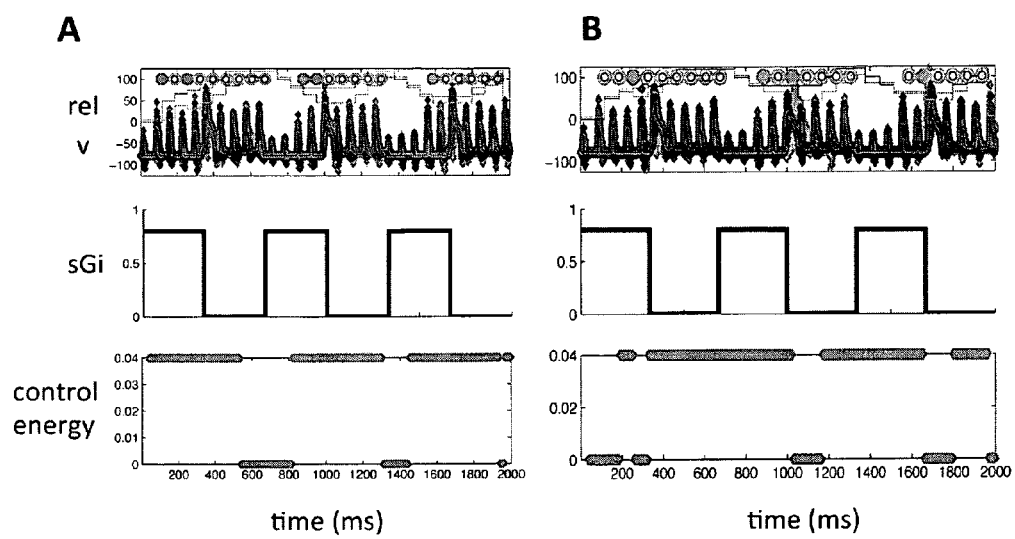

FIG. 10 shows an example of control of TC reduced cell model using reliability as a control parameter. In A is shown a threshold of turning on GPi stimulation when reliability<0.9. In B is shown a different strategy, using an inverse approach. In B control is turned on when reliability is >0.5. Note that the relevant reliability in both examples is the controlled piecewise continuous line in the upper panel with the uncontrolled result shown for comparison. The inherent delays in employing the moving average of reliability can be exploited so that inverse reliability control can be more reliable than using a more intuitive strategy based on turning on stimulation when reliability falls.

Figure 11:
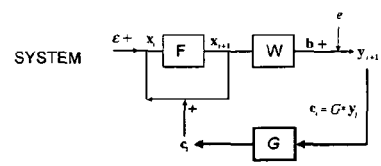
Figure 11:
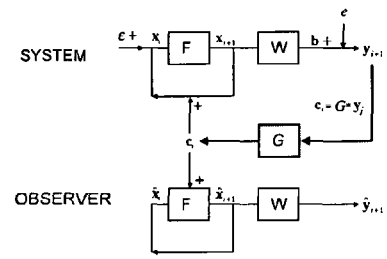
Figure 11:
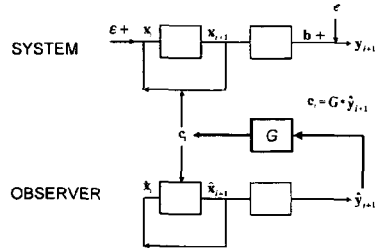
Figure 11:
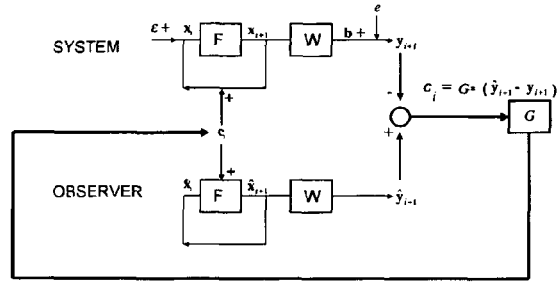

FIG. 11 shows the logic of placing a model-based observer within the control scheme. In A, we show a typical prior art controller. The measurements, y, reflect some modification by the processes W, which always shield us from the underlying true variables x which are evolving along the prescribed dynamics F at times i. We assume that there is noise and uncertainty represented by e and $\epsilon$ inserted at the level of the process F and the measurements y respectively. We show a typical prior art control law, G, which may be an arbitrary linear or nonlinear control law, which operates upon the measured variables y, which may undergo a degree of signal processing or conditioning before insertion into the control law itself. The feedback is directed back to the natural system F being observed. The control laws used in prior art use are often proportional or a proportional variant (proportional-integral-differential). In B, we show how one may place a fundamental model of the natural system as an observer, and feed it the same control that the system is receiving. This would permit one to better estimate and observe what is happening within the natural system variables x, but would not improve control. More effective, and the subject of this present invention, is as shown in C to use the observer system to determine the control. One can then use the observer system as a filter, stripping out noise and uncertainty, and accurately estimating what is happening within the natural system. One then controls the model, delivering the control vector c to both model and natural system. When the control observer is a good one, the natural system synchronizes to the model, and both are controlled simultaneously while one has full access to the dynamics of the observer system. In D we show a variant of such model based control, where a differential measurement between the natural system y and the control observer measurement y are used in the control law. One might here envision that the observer model is a healthy model, attached to a diseased organ such as a Parkinsonian brain, and the differential measurement is part of the control law used to control both the model and the natural system. Again, when the model observer is a good one, the two systems will synchronize.

Figure 12:
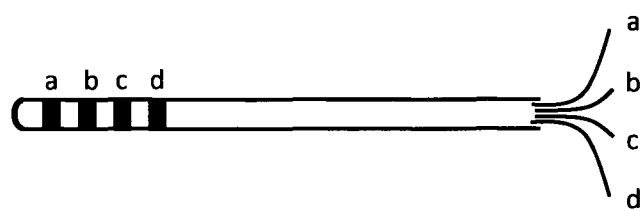

FIG. 12 shows an example of a typical sensor for a model-based control system. This particular example is an electrode with a single shaft, that contains multiple contacts. One of more of these contacts can be used for measurements of voltage, which requires pairs of electrodes, although one electrode can be a distant reference not in the brain, and one or more electrodes for passing electrical current. Again, the current passing electrodes need to be in pairs, unless there is a distant return electrode as part of the device not in the brain. The point is that model-based control let's one minimize the points within the brain that sensing is performed, and where control is applied. The fundamental model permits us to reconstruct from these sparse measurements what the rest of the relevant part of the brain is doing, as well as examine the response of the brain system to isolated control delivered to a particular structure with, for instance, a single electrode. Although an electrode sensing and current delivery system is shown, in practice other forms of chemical, thermal, or ionic sensing can be used, and the fundamental model used to reconstruct the activity of the system. Similarly, the current delivery can be replaced by ionic or drug delivery, or even magnetic fields delivered, and again, the effects of the control perturbations delivered tracked by the model observer to which the same control maneuvers are applied as shown in FIG. 11.

SUMMARY OF THE INVENTION

This is a proposal to fuse fundamental computational models of a part of the brain that requires control, along with nonlinear control engineering theory.

By fundamental computational model, we mean a model that is constructed to embody, in mathematical terms, the actual underlying biology, biophysics, and physics of the system to be controlled.

The features part of a fundamental model of the brain includes the ions such as potassium, sodium, chloride, and calcium, whose concentrations and flow from one compartment to another within and between neurons determines the individual cell and network excitability and electrical activity. The geometry of individual neurons is part of a fundamental model. The topology of the interconnectivity of the cells, through their synaptic connections, as well as the electrical connectivity through ephaptic effects, is part of a fundamental model. The connectivity of regions of the brain, such as nuclei comprising similar types of neurons and groups of neurons, and cortical regions defined by anatomy or function, or regions of the brain stem or cerebellum, comprise the components of a fundamental model. Prior art has not envisioned such fundamental features as necessary components of model-based brain control.

We distinguish models of the fundamental biology and physics from standard empirical models which are based on statistical descriptions of data recorded from a system, or upon theoretical descriptions of processes which are not reflective of the underlying biology and physics. An example of the latter are frequency decompositions of data into sines and cosines when the underlying natural system is not an ensemble of sine and cosine generators.

Fundamental computational models of Parkinson's disease suitable for use in model-based control schemes have only been available since 2004.

The use of fundamental computational models of neuronal systems from the brain requires the use of true nonlinear control filters to absorb or assimilate data. Such filters have generally been embodied as ensemble filters, where to preserve the nonlinearities of the fundamental model, the filters preserve the nonlinear equations, and multiple solutions are handled at the same time (this is the ensemble part). Such filters are in common use in robotics and numerical weather prediction. They have never been used for Parkinson's or other related dynamical disease of the brain.

The difference between the use of a fundamental model is that the controller actually emulates the behavior of the natural system. The controller, through use of it's data assimilation filter, actually reconstructs the natural system dynamics, through its model that emulates the natural system components, even though the number of measurements of those components are actually sparse and limited. This is always the case in the brain, where billions of neurons contribute to activity, and even arrays of measurement electrodes always is relatively sparse compared with the complexity of the system.

Because fundamental models emulate the natural system, when performing well they synchronize to the natural system. One can then control the model, and the natural system will follow along closely and be controlled.

A synchronized fundamental model is predictive. That is, it will predict the natural system's dynamics because it embodies the natural system's dynamics. Predictive control is always better than non-predictive control.

Prediction in a fundamental model is quite different from prediction as typically used in brain feedback devices (such as U.S. Pat. No. 2009/0018609 a1 (DiLorenzo)). One can construct an infinite variety of predictive schemes for natural systems based on empirical data analysis, or upon hypotheses related to such empirical data analysis. For instance, one might predict that a seizure will occur if a certain combination of frequencies are observed in the data. Such schemes are in contrast to the use of fundamental models where the model itself acts like the natural system, and efficient model-based control schemes adjust themselves iteratively based on their errors of prediction. A model-based control scheme constantly predicts what the natural system will do, and this prediction is repeatedly contrasted with the actual measurement and reconstruction of the natural system dynamics. It uses these errors, call the innovations, to continually tune the parameters of the model-based control system in order to optimally track the natural system. This tuning is necessary to compensate for the fact that all models are imperfect replicas of natural systems (called model inadequacy), and because there are variables that are unexpected and not taken into account in the models (such as gusts of wind for an airplane model). The predictive nature of such model-based schemes always makes them better than any scheme that tunes itself to the present state or past observations of a natural system—model-based control schemes tune themselves adaptively to prediction of the future.

Many controllers use predictive schemes. One can, in a seizure predictor, use empirical tests and statistics to estimate whether a seizure is likely to occur in the future. In contrast, in a model-based control scheme, if a seizure is starting in the model, it is starting in the natural system. In terms of Parkinson's disease, the frequencies that one wishes to control are actually exhibited in the model, and by controlling the model, one suppresses similar frequencies in the natural system. Although one might apply empirical schemes to predict what the model dynamics might mean or predict, the model and system are dynamically fused in a way most distinct from typical embodiments of empirical non-model-based control schemes.

Because of the efficiency of model-based control schemes, the amount of energy used to create a controller is typically much less than the energies required without an accurate fundamental model. An important reason for this energy reduction is that the fundamental model acts as a filter, helping to strip out noise and measurement error in the process of the reconstruction of the underlying natural system's dynamics. The control law used is then not fluctuating with the amplitude of noise and measurement error effects as it would otherwise fluctuate. Thus model-based control schemes are energy efficient.

Model-based control schemes actually use noise, in contrast to non-model based control schemes where noise must be eliminated. One way noise is used is by injecting it in the estimation step of the next measurement of the natural system. In a model-based navigation scheme, one predicts where a boat will be on the ocean at a time in the future. One then injects noise into this prediction so that the prediction is not a point, but rather a ring of points that encloses an area of uncertainty within which it is likely to have captured the true location. Too much noise ensures that the location is always captured, but the degree of uncertainty renders such a prediction useless. Therefore, we adaptively adjust the noise injected into our model-based observer to optimally track the natural system. Another reason to inject noise, is that the typical ensemble Kalman filter used in such controllers have a tendency to reduce their uncertainty over time—again, noise is injected into the fundamental model itself within such filters in order to stabilize them.

In this present invention, in contrast to other embodiments of brain control devices, we will inject noise into the controller in order to both stabilize the observer filter, as well as to optimize tracking errors.

Synchronizing controllers also permit us to run multiple copies of the model-based observer in parallel. Synchrony implies that if one starts two systems with different initial conditions, that each forgets their initial conditions, and synchronizes to each other. A unique strategy to then tell whether a natural system is changing is to start off multiple copies of a model observer at different times with different initial conditions and see if the models synchronize to the natural system and to each other. Loss of such rapid synchronization tells us that the models are no longer synchronizing to the natural system. Since in real use with the brain, we never know the true state of the brain variables, we only estimate them, we can watch the model systems, which we have completely specified, and ask whether they are synchronizing to each other. Loss of such synchronization implies that the models have lost their synchronization with the natural system that we imperfectly know. Loss of such synchronization is a powerful means of prediction of changes of state of the underlying brain system. This is useful to suggest that a model needs to be switched, perhaps as a function of sleep stage, or that a patient's drug levels have changed. It is also useful in brain diseases with rare events, such as in seizures, where such loss of model synchronization may imply that a seizure is imminent.

As implied by our discussion of synchrony, model-based controllers require a suitable set of initial conditions to be able to track or synchronize to a natural system or to another model observer. Once running, the estimate from the prior step is typically used as an initial condition. But the device must be started with a suitable range of initial conditions, and constraints need to be placed upon the initial conditions for future steps of the estimating filter so that the tracking will be useful and the filter will remain stable.

It is important to note that the suitable initial conditions are not necessarily the same as physically plausible ones. Because all models are imperfect emulations of reality, the optimal tracking of such observer models may typically require use of ranges of variables and parameters which are not biologically or physically plausible. The extent of the range of such variables and parameters to deviate from natural ranges is dependent upon the filter stability.

This invention is dependent upon fundamental models, but the precise fundamental models used may be changed. As new knowledge is gained about the biology and physics of a system, refinements and additions to fundamental models are made. But the goal of this invention is optimal control, not reengineering of nature. Adding components of a model that are not strongly modulating the dynamics we seek to control may be realistic, but will hurt controller performance if it adds computational complexity and adds additional uncertainty to the iterative model predictions, without a comparable improvement in device performance.

A further subtle aspect of our fundamental models is that they must emulate nature. But the features of nature to emulate are their dynamical behavior—their physics—not each biological detail. One needs to start with the biological details to preserve the natural system qualities. But a progressive reduction in model complexity, preserving the physics and eliminating needless biological complexity, is important to seek.

All fundamental models of Nature are imperfect replicas of Nature. As such, we need to address model inadequacy properly. One way to do this is through local mean field approximations of model parameters utilizing methods such as the consensus set. Another powerful strategy is to incorporate formal parameterization using inadequacy parameters for each relevant variable. The optimization for such inadequacy parameters can be performed outside of the ensemble Kalman filter equations, rather than adding them to the state variables as an augmented state.

Similarly, it is important to eliminate mathematical symmetries from the fundamental models in order for them to work well in this invention. Nature, for instance, often uses multiple currents in brain cells that have similar time courses and functions. Such redundant features of biology are helpful for evolution, but introduce uncertainty in model observers. We thus need to reduce our complex models to eliminate mathematical symmetries in the models and reduce their tracking errors.

The use of model-based controllers for brain disease must recognize that the quality of tracking and observation—the innovations—are intimately related to the range of control possible—the reachability. A key feature of this is how many measurement points in space need to be utilized by a model-based controller. Ideally, one only places 1 electrode within the brain or onto the brain, minimizing hazard to the patient. But a second measurement probe may give dramatically improved tracking and observation, and the risk may be worth the potential benefits in such medical device decision making.

Because a model-based controller can reconstruct variables within a natural system that are not directly measured or accessed, there is freedom to chose pertinent observable variables. One can use electrical measurements and reconstruct metabolic variables and ion levels for instance within the brain. On the contrary, one might measure the level of a particular brain chemical or an ion concentration, and reconstruct the electrical activity of the brain. Which variable or combination of variables to measure depends upon our sensing technology available, the risk of the use of a given sensing measurement technology, and the mathematical quality of the fundamental model to reconstruct unobserved variables from those observable variables that it does have measurement access to.

DETAILED DESCRIPTION OF THE INVENTION

This device is a fusion of a fundamental computational model that embodies the biology and physics of part of the brain, with a nonlinear control framework that consists of a data assimilation front end filter, and a specified control law. The control laws employed are typical prior art proportional-integral-differential, or variable state or sliding mode control laws. The novel part of this invention is the use of a fundamental model to observe, reconstruct, and track brain activity.

Figure 2:
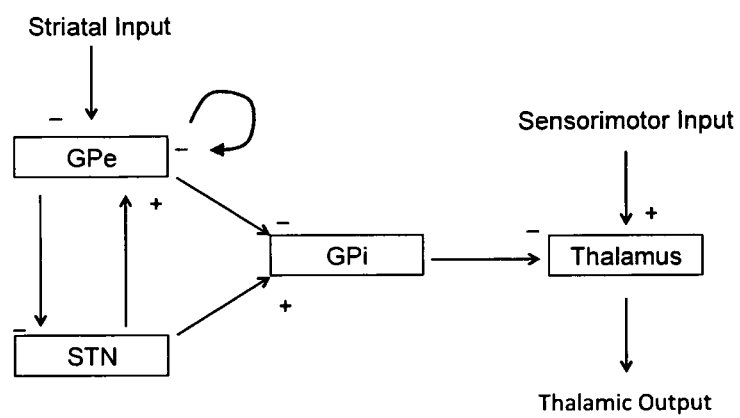
FIG. 2 is a schematic of rhythm generating structures in Parkinson's disease. Striatal input refers to the outer segments of the basal ganglia that send input to these deeper segments. Excitatory input refers to sensorimotor input to the thalamus that needs to be relayed to cortex. Excitation, +, and inhibition, −.
Figure 3:
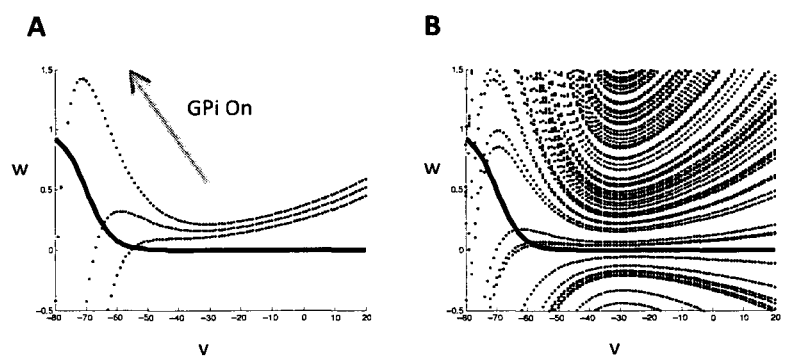
FIG. 3 shows nulclines for w (thick line) and v (dotted line). In A, with increased GPi inhibition onto the reduced TC cell, the v nullcline is elevated with respect to the w nullcline. In B are shown reconstruction estimates of the nullclines from noisy measurements.
Figure 4:
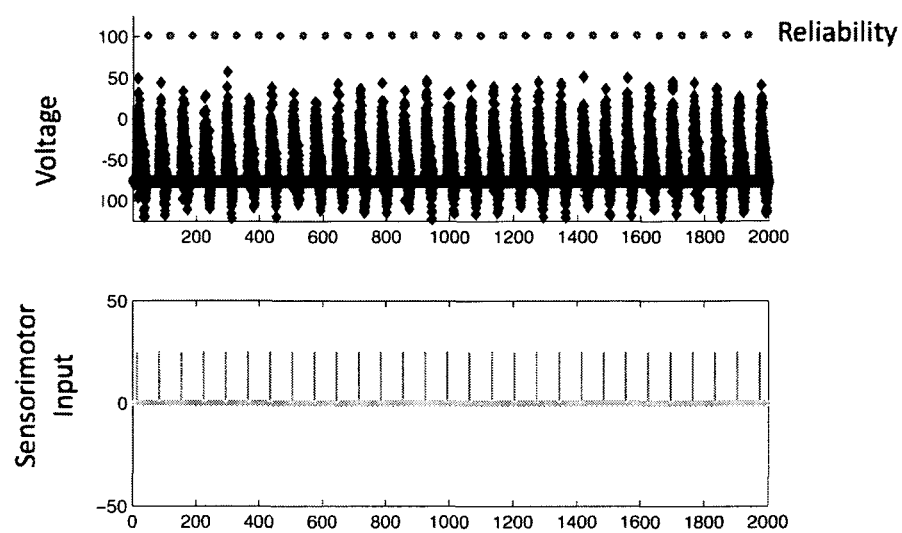
FIG. 4 shows normal response of TC cell to periodic sensorimotor stimulation. Voltage in reduced TC cell model (thin line, upper panel), with substantial added noise to serve as a noisy observable (markers, upper panel), and sensorimotor input (pulses, lower panel). Each time a sensorimotor pulse is reliably transmitted, a marker is placed above the successfully transmitted spike. This cell is 100% reliable.
Figure 5:
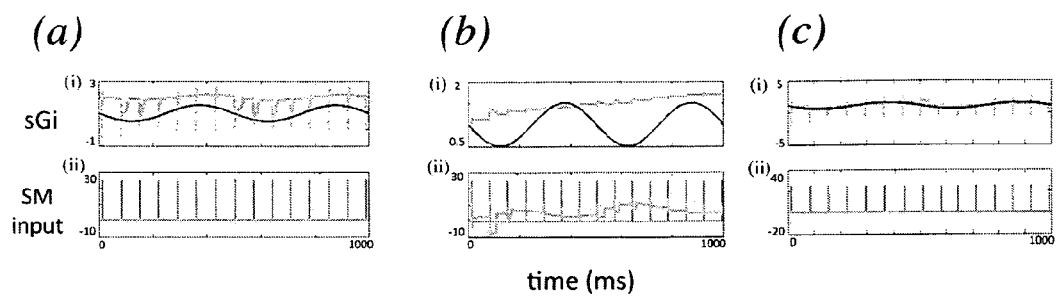
FIG. 5 shows an example of assimilating TC cell voltage (top row). Estimates of w, synaptic current from GPi (middle row, sGi), and sensorimotor input (bottom row, SM input).

For use in Parkinson's disease, the fundamental model will model the structures of the brain relevant to the control of signs and symptoms of the disease, including the structures illustrated in FIG. 2 such as subthalamic nucleus, globus pallidus (interna and externa), striatum (putamen and caudata nuclei), thalamus, cortex, cerebellum, and other structures as needed to represent relevant activity.

Figure 1:
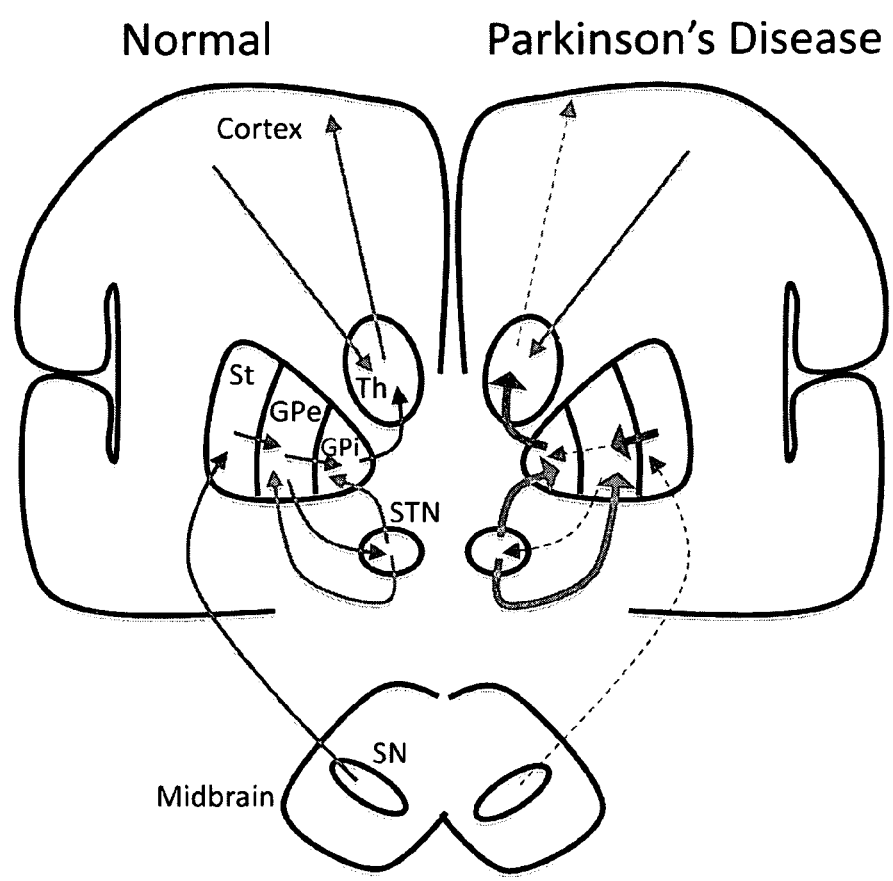
FIG. 1 is a schematic of network imbalance in Parkinson's disease. The contrast with normal in the Parkinson's disease state is shown on the right, where thickened (thinned) lines indicate an increase (decrease) in excitation or inhibition. St: striatum, GPe: globus pallidus externa, GPi: globus pallidus interna, Th: Thalamus, STN: subthalamic nucleus, and SN: substantia nigra.

For use in Parkinson's disease, the fundamental model will incorporate compartmental computational models representing the dynamics and geometry of the relevant neurons within the structures mentioned above, using equations such as represented in equations (1)-(14). Such equations will represent compartments such as the cell body or soma, and the dendrites, often with apical and basal dendrites, as well as the axons carrying the output signals from one neuron to another. In addition, the dynamics of the extracellular space, and the ion fluxes within that space, is a critical one for such models, and must be incorporated along with the models of the neuronal compartments themselve. The glia cells form an intimate link to the extracellular space dynamics, as well as the microvasculature that forms the source and sink for the ions and chemical species that determine the dynamics and excitability of such neuronal models. The equations for the neurons, with the topology of their connections specified, is then collected as the network models that represent the connectivity of the various structures as specified in FIG. 1 or FIG. 2.

FIG. 11A shows a typical prior art control scheme. The measurements are taken directly from the natural system, or brain in this case, and perhaps with a variety of empirical signal conditioning or processing, are inserted into the control law G, which may be linear or nonlinear, and used to direct control, which may be electrical, magnetic, or chemical, back to the natural system itself.

FIG. 11C shows an embodiment of the present invention, where an observer system, composed of a fundamental model of the underlying natural system, generates the measurements ŷ, or the underlying estimate of the true variables, x̂, that are used in the control law G. The control signal c is then fed back to both the model and the natural system. The fundamental model and natural system synchronize—by controlling the model, the natural system is controlled. The noise and uncertainty that are part of the natural system, as shown in e and ϵ, are filtered out by the observer model. The ability to perform this type of observer control for the brain was dependent upon learning enough about the brain to form computational models with sufficient fidelity to accurately represent the dynamics of the parts of the brain in question, as well as nonlinear ensemble control frameworks that could handle the nonlinearity and complexity of such fundamental models within a control device, and these availabilities of such models and controllers are relatively recent and thus absent and not envisioned within prior art.

FIG. 11D shows a variation upon the model based controller, using the differential signal between measurements of the natural system and model in the control law. When constructing a model-based controller for a brain disease, one may wish to run a model that represents the same parts of the healthy brain, in order to seek to synchronize the diseased parts of the brain represented in the model to a healthy state dynamic.

A typical sensor and control effector is illustrated in FIG. 12. Such a sensor and effector would ideally be constitute a single shaft if it is to be inserted into the brain, and contain multiple contacts. If electrical, at least 2 contacts would typically be used for sensing voltage. If electrical, at least 2 contacts would typically be used for passing current. Both functions would take place simultaneously. Such electrodes are prior art, but the present invention permits one to minimize the number of sensors and effectors used, since the fundamental model reconstructs what is happening at other points within the relevant brain structures, and models the effect of control signals placed at a restricted location or set of locations within the brain by driving the model with the identical control signals.

Multiple observer models can be used at the same time, and is a desirable feature of model based control. For instance, in FIG. 11C and FIG. 11D, one would use multiple observer systems running simultaneously for a variety of purposes. One purpose is to start the same model at different times, with the most recent estimate of the state variables x, to see if the models rapidly synchronize, or diverge, from each other. This tests whether the natural system is changing, or if the model being used is still a good reflection of the parts of the brain being observed and tracked. In a similar fashion, one can deliberately run several different models simultaneously, seeking to see which model is, at any given time, a better reflection of the underlying natural system. Reasons to run a variety of different models would include to see if a model representing various states of sleep or wakefullness were best. Different models may represent the on-off states that Parkinson's disease patients get into depending on how long it has been since they have last taken their medication. In an epilepsy device, different models may represent the time between seizures (interictal), the time during seizures (ictal), and importantly, the state just before an impending seizure (preictal).

The model based controller can just as readily work with reconstructing and observing the dynamics, and directing control, if a superficial part of the brain is sensed using, for instance, typical prior art subdural electrodes or cortical electrode microelectrode arrays. One can place such electrodes in an epidural location, or within or without the skull if desired. Interposing dura, or skull, or scalp between sensors and the brain structures to be measured, will require an accurate model of these intervening structures to be incorporated within the model as well.

All observer models require initial conditions to be provided in order to initiate tracking and observation of a system. Typical initial conditions for relevant variables would, for instance, entail constraints to lie within ranges of ion concentrations for essential variables such as Extracellular Sodium=40 to 200 millimolar.
Extracellular Potassium=0.1 to 100 millimolar.
Intracellular Sodium=0.1 to 100 millimolar.
Intracellular Potassium=10 to 200 millimolar.
Extracellular Calcium=0.01 to 10 millimolar.
Intracellular Calcium=0.01 micromolar to 10 millimolar.
Transmembrane voltage=−100 to 150 millivolts.
Intracellular Chloride=1 to 150 millimolar.
Extracellular Chloride=1 to 250 millimolar.

I claim:

1. A computer-based mechanical system for controlling unwanted neurological behavior in an animal or human, comprising:
    a) at least one electrode or sensor;
    b) at least one computer processor; and
    c) a computer, said computer containing a program further containing computational brain models and nonlinear ensemble filters, said computational models further comprising separate models for observation and control with said separate models being capable of operating in intercommunicating parallel, wherein said separate models are in constant feedback communication with one another and with said at least one electrode or sensor.

2. The computer based mechanical system according to claim 1 wherein said separate models further comprise at least three distinct models and the system selects and applies one of said distinct models by assessing which model synchronizes best to a brain being sensed by the electrode or sensor and further which generates the smallest tracking error compared to the other distinct models.

3. The computer based mechanical system according to claim 2 wherein electrical signals within the brain are measured by at least one or more electrodes adapted to be placed in a location selected from the group consisting of the thalamus, globus pallidus, striatum, subthalamic nucleus, cerebellum, brain stem, spinal cord, peripheral nerve, muscle and cortex.

4. The computer based mechanical system according to claim 3 wherein said unwanted neurological behavior is attributable to a disease selected from the group consisting of Parkinson's disease, epilepsy, cognitive disorders, depression, obsessive compulsive disorder, posttraumatic stress disorder, states of wakefulness, minimally conscious state, persistent vegetative state, disorders of digestion or ingestion, disorders of craving, obesity, anorexia, drug addiction, disorders of attention, and attention deficit disorder.

* * * * *